(12) United States Patent
Otto et al.

(10) Patent No.: US 8,524,862 B2
(45) Date of Patent: Sep. 3, 2013

(54) MUTEINS OF C5A ANAPHYLATOXIN AND METHODS OF INHIBITING C5A

(75) Inventors: Magnus Otto, Hannover (DE); Jörg Köhl, Cincinnati, OH (US)

(73) Assignee: Cincinnati Children's Hospital Medical Center, Cincinnati, OH (US)

( * ) Notice: Subject to any disclaimer, the term of this patent is extended or adjusted under 35 U.S.C. 154(b) by 2320 days.

(21) Appl. No.: 10/508,376

(22) PCT Filed: Mar. 19, 2002

(86) PCT No.: PCT/EP02/03035
§ 371 (c)(1),
(2), (4) Date: Jun. 28, 2005

(87) PCT Pub. No.: WO03/078457
PCT Pub. Date: Sep. 25, 2003

(65) Prior Publication Data
US 2006/0052294 A1  Mar. 9, 2006

(51) Int. Cl.
*A61K 38/16* (2006.01)
*C07K 14/47* (2006.01)

(52) U.S. Cl.
USPC .......................... 530/350; 514/12.2; 514/21.3

(58) Field of Classification Search
None
See application file for complete search history.

(56) References Cited

U.S. PATENT DOCUMENTS

| | | | |
|---|---|---|---|
| 5,506,121 A | 4/1996 | Skerra et al. |
| 5,696,230 A | 12/1997 | Sanderson et al. |
| 5,807,824 A | 9/1998 | van Oostrum et al. |
| 5,942,599 A | 8/1999 | Sanderson et al. |
| 6,022,951 A | 2/2000 | Sano et al. |

FOREIGN PATENT DOCUMENTS

WO   WO 99/00406 A1   1/1999

OTHER PUBLICATIONS

Otto et al., J. Biol. Chem. 279: 142-151, 2004.*
Cain et al., Biochemical Pharmacology 61: 1571-1579, 2001.*
Cain et al., Protein Engineering 14: 189-193, 2001.*
Hennecke, M., Untersuchung zur C5a-C5a Rezeptor-Interaktion unter Verwendung des Phage-Displays, PhD thesis, 1998, Medical School Hannover, Germany.
Heller, T. et al., C5a mutant selected from a phage library is a potent C5a-receptor antagonist in vitro and in vivo, Molecular Immunology, Apr. 1998, vol. 25, No. 6-7.
Heller T., et al, Selection of a C5a receptor antagonist from phage libraries attenuating the inflammatory response in immune complex disease and ischemia/reperfusion injury, Jul. 15, 1999, pp. 985-994, vol. 163, No. 2, Journal of Immunology.
Hennecke, M. et al., A detailed analysis of the C5a anaphylatoxin effector domain: Selection of C5a phage libraries on differentiated U937 cells, Feb. 1998, pp. 36-44, vol. 252, No. 1, European Journal of Biochemistry.
Pellas et al., Novel C5a receptor antagonists regulate neutrophil functions in vitro and in vivo, Journal of Immunology, Jun. 1, 1998, pp. 5616-5621, vol. 160, No. 11.
Toth, M. et al., The pharmacophore of the human C5a anaphylatoxin, 1994, p. 1164, vol. 3, No. 8, Protein Science.
Anderson, C. et al., C5aR ligand peptide 3D QSAR study performed with an applied linear conformation, 1997, pp. 476-483, vol. 49, No. 6, Journal of Peptide Research.
Kinoshita, T., Overview of Complement Biology, 1991, pp. 291-300, vol. 12, Immunology Today.
Müller-Eberhard, H.,Molecular organization and function of the complement system, 1988, pp. 321-347, vol. 57, Annu. Rev. Biochem.
Gerard, C. & Gerard, N.P., C5a anaphylatoxin and its seven transmembrane-segment receptor, 1994, p. 775, vol. 12, Ann. Rev. Immunol.
Köhl, J. & Bitter-Suermann, D., Ch. 11 Anaphylatoxins, 1993, pp. 299-324, Anaphylatoxins in Complement in Health and Disease, 2nd Ed., Whaley et al., Eds., Kluwer Academic Publisher, Dordrecht.
Ember, J. et al., Ch. 11 Characterization of complement anaphylatoxins and their biological responses, 1998, pp. 241-284, Human Complement in Health and Disease, Volkanis & Frank, Eds., Marcel Dekker, New York.
Czermak, B. et al., Protective effects of C5a blockage in sepsis, 1999, pp. 788-792, vol. 5:7, Nature Medicine.
Bautsch, W. et al., Cutting Edge: Guinea pigs with a natural C3a-receptor defect exhibit decreased brochoconstriction in allergic airway disease, 2000, pp. 5401-5405, vol. 165, J. Immunol.
Humbles, A. et al., A role for the C3a anaphylatoxin receptor in the effector phase of asthmas, 2000, pp. 998-1001, vol. 406, Nature.
Karp, C. et al., Identification of complement factor 5 as a susceptibility locus for experimental allergic asthma, 2000, pp. 221-226, vol. 1:3, Nature Immunol.
Bautsch, W. et al., A recombinant hybrid anaphylatoxin with dual C3a/C5a activity, 1992, pp. 261-266, vol. 288, Biochem. J.
Haslett, C. et al., Cessation of neutrophil influx in C5a-induced acute experimental arthritis is associated with loss of chemoattractant activity from the joint space, 1989, pp. 3510-3517, vol. 14:10, J. Immunol.
Krug, N. et al., Complement factors C3a and C5a are increased in brochoalveolar lavage fluid after segmental allergen provocation in subjects with asthma, 2001, pp. 1841-1843, vol. 164, J. Respir. Crit. Care Med.
Mollison, K. et al., Identification of receptor-binding residues in the inflammatory complement protein C5a by site-directed mutagenesis, 1989, pp. 292-296, vol. 86, Proc. Natl. Acad. Sci. USA.
Baumann, U. et al., A codominant role of FcγRI/III and C5aR in the reverse arthus reaction, 2000, pp. 1065-1070, vol. 165, J. Immunol.
Köhl, J., Ch. 8, The anaphylatoxins, 1997, pp. 135,163, Complement: a practical approach, Dodds & Simm, Eds., IRL Press, Oxford.

(Continued)

*Primary Examiner* — Philip Gambel
(74) *Attorney, Agent, or Firm* — Frost Brown Todd LLC

(57) ABSTRACT

The present invention refers to muteins of the C5a anaphylatoxin (C5a) which are C5a receptor antagonists, to nucleic acid molecules comprising a nucleotide sequence encoding such muteins of C5a anaphylatoxin, to host cells containing a nucleic acid molecule comprising a nucleotide sequence encoding such muteins of the C5a anaphylatoxin as well as to a pharmaceutical composition comprising a mutein of the C5a anaphylatoxin acting as a C5a receptor antagonists. A mutein of the invention is a C5a receptor antagonist wherein the amino acid residue naturally occurring at sequence position 69 is mutated.

12 Claims, 5 Drawing Sheets

(56) References Cited

OTHER PUBLICATIONS

Figure 3:
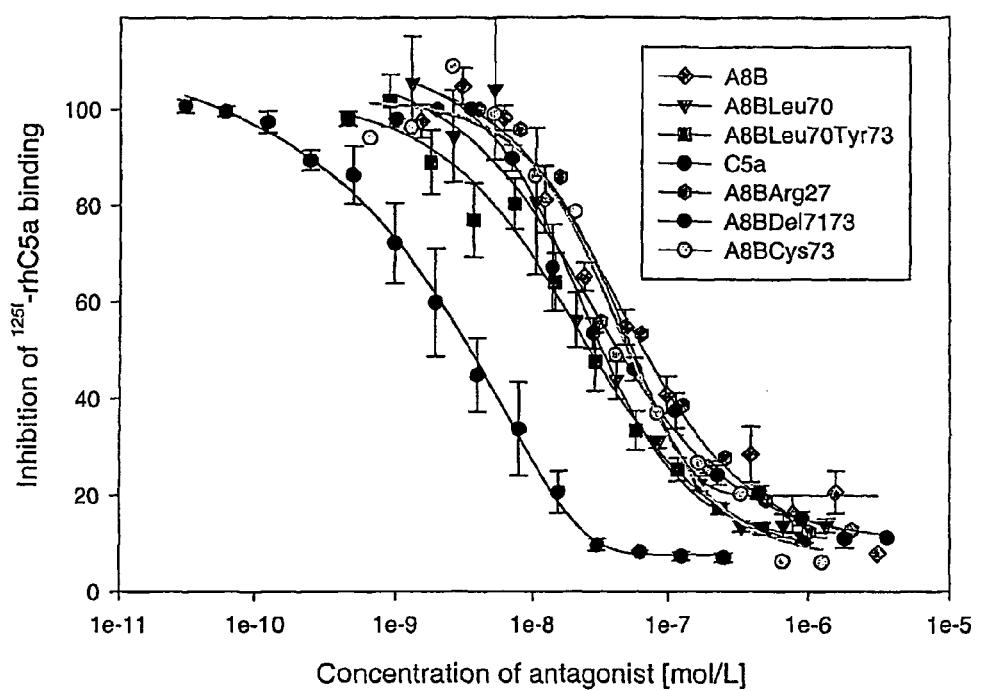

Bock, D. et al, The C terminus of the human C5a receptor (CD88) is required for normal ligand-dependent receptor internalization,nC terminus of the human C5a receptor (CD88) is required for normal ligand-dependent receptor internalization,n 1997, pp. 1522-1529, vol. 27, Eur. J. Immunol., 27.

Seligmann, B. et al., Fluorometer based multi-parameter analysis of phagocytic cell activation, , 1987, pp. 375-378, vol. 21, Agents and Actions.

Cain, S. et al., analysis of receptor/ligand interactinos using whole-molecule randomly-mutated ligand libraries, 2000, pp. 139-145, vol. 245, J. Immunol. Methods.

Haugland, R., Handbook of Fluorescent Probes and Research Chemicals, 6th Ed., 1996, pp. 69-70, Molecular Probes, Inc., Eugene, OR.

Remington's Pharmaceutical Sciences, 15th Ed., 1975, Mack Pub., Easton, PA, pp. iii, iv, xi.

Baneyx, F., Recombinant protein expression in *Escherichia coli*, 1999, pp. 411-421, vol. 10, Curr. Opin. Biotechnol.

Makrides, S., Components of vectors for gene transfer and expression in mammalian cells, 1999, pp. 183-202, vol. 17, Prot. Expr. Purif.

Cereghino, J. & Cregg, J., Heterologous protein expression in the methylotrophic yeast *Pichia pastoris*, 2000, pp. 45-66, vol. 24, FEMS Microbiol. Rev.

Colosimo, A. et al., Transfer and expression of foreign genes in mammalian cells, 2000, pp. 317-318, vol. 29, No. 2, Biotechniques.

Bautsch, W. et al., Human C5a Anaphylatoxin: Gene closing and expression in *Escherichia coli*, 1992, pp. 41-52, vol. 185, Immunobiology.

Crameri, R. & Suter, M., Display of biologically active proteins on the surface of filamentous phages: a cDNA cloning system for selection of functional gene products linked to the genetic information responsible for their production, 1993, pp. 69-75, vol. 137, Gene.

Barbas III, C. et al., Assembly of combinatorial antibody libraries on phage surfaces: the gene III site, Sep. 1991, pp. 7978-7982, vol. 88, Proc. Natl. Acad. Sci. USA.

Klos. A. et al., Detection of native human complement components C3 and C5 and their primary activation peptides C3a and C5a (anaphylatoxic peptides) by ELISAs with monoclonal antibodies, 1988, pp. 241-252, vol. 111, J. Immunol. Methods.

Hennecke, M. et al., A selection system to study C5a-C5a-receptor interactions: Phage display of a novel C5a anaphylatoxin, Fos-C5a$^{Ala27}$, 1997, pp. 263-272, vol. 184, Gene.

Otto, M. "C5a Mutants Are Potent Antagonists of the C5a Receptor (CD88) and of C5L2,"Jan. 2, 2004, pp. 142-151, vol. 279, No. 1, The Journal of Biological Chemistry.

Hennecke, M. "Unterscuchung zur C5a-05a Rezeptor-Interaktion unter Verwendung des Phage-Displays," PhD thesis, 1998.

English Translation of: Hennecke, M. "Unterscuchung zur C5a-05a Rezeptor-Interkation unter Verwendung des Phage-Displays," PhD thesis, 1998.

\* cited by examiner

```
3'- ATGACGCTGCAAAAGAAGATAGAAGAAATAGCTGCTAAATATAAACATTCA
NH2- MetThrLeuGlnLysLysIleGluGluIleAlaAlaLysTyrLysHisSer

GTAGTGAAGAAATGTTGTTACGATGGAGCCTGCGTTAATAATGATGAA
     ValValLysLysCysCysTyrAspGlyAlaCysValAsnAsnAspGlu

ACCTGTGAGCAGCGAGCTGCACGGATTAGTTTAGGGCCAAGATGCATC
     ThrCysGluGlnArgAlaAlaArgIleSerLeuGlyProArgCysIle

AAAGCTTTCACCGAATGTTGTGTCGTCGCAAGCCAGCTCCGTGCTAAT
     LysAlaPheThrGluCysCysValValAlaSerGlnLeuArgAlaAsn

ATCTCTCATAAAGACATGCAATTGGGAAGG
     IleSerHisLysAspMetGlnLeuGlyArg
```

Fig. 1

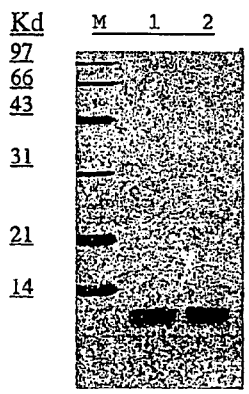

Fig. 2

SEQUENCE LISTING

<160> NUMBER OF SEQ ID NOS: 49

<210> SEQ ID NO 1
<211> LENGTH: 222
<212> TYPE: DNA
<213> ORGANISM: Homo sapiens
<220> FEATURE:
<223> OTHER INFORMATION: coding sequence of recombinant human C5a
      (rhC5a)

<400> SEQUENCE: 1

```
acgctgcaaa agaagataga agaaatagct gctaaatata aacattcagt agtgaagaaa      60
tgttgttacg atggagcctg cgttaataat gatgaaacct gtgagcagcg agctgcacgg     120
attagtttag ggccaagatg catcaaagct ttcaccgaat gttgtgtcgt cgcaagccag     180
ctccgtgcta atatctctca taaagacatg caattgggaa gg                        222
```

<210> SEQ ID NO 2
<211> LENGTH: 219
<212> TYPE: DNA
<213> ORGANISM: Artificial Sequence
<220> FEATURE:
<223> OTHER INFORMATION: mutant(c5a-(Cys27Ala)-A8B of human C5a

<400> SEQUENCE: 2

```
acgctgcaaa agaagataga agaaatagct gctaaatata aacattcagt agtgaagaaa      60
tgttgttacg atggagccgc cgttaataat gatgaaacct gtgagcagcg agctgcacgg     120
attagtttag ggccaagatg catcaaagct ttcaccgaat gttgtgtcgt cgcaagccag     180
ctccgtgcta atatctcttt taaaaggtcg ctgttgcgt                            219
```

<210> SEQ ID NO 3
<211> LENGTH: 219
<212> TYPE: DNA
<213> ORGANISM: Artificial Sequence
<220> FEATURE:
<223> OTHER INFORMATION: artificial sequence of mutant
      (C5a-(1-66,Cys27Ala)-A8B-Leu70 of human C5a

<400> SEQUENCE: 3

```
acgctgcaaa agaagataga agaaatagct gctaaatata aacattcagt agtgaagaaa      60
tgttgttacg atggagccgc cgttaataat gatgaaacct gtgagcagcg agctgcacgg     120
attagtttag ggccaagatg catcaaagct ttcaccgaat gttgtgtcgt cgcaagccag     180
ctccgtgcta atatctcttt taaaaggctg ctgttgcgt                            219
```

<210> SEQ ID NO 4
<211> LENGTH: 213
<212> TYPE: DNA
<213> ORGANISM: Artificial Sequence
<220> FEATURE:
<223> OTHER INFORMATION: mutant (C5a-(1-66, Cys27Ala) -A8B-Cys71 of
      human C5a

<400> SEQUENCE: 4

```
acgc tgcaaaagaa gatagaagaa atagctgcta aatataaaca ttcagtagtg             54
aagaaatgtt gttacgatgg agccgccgtt aataatgatg aaacctgtga gcagcgagct     114
gcacggatta gtttagggcc aagatgcatc aaagctttca ccgaatgttg tgtcgtcgca     174
agccagctcc gtgctaatat ctcttttaaa aggtcgtgt                            213
```

```
<210> SEQ ID NO 5
<211> LENGTH: 219
<212> TYPE: DNA
<213> ORGANISM: Artificial Sequence
<220> FEATURE:
<223> OTHER INFORMATION: mutant (C5a-(1-66,Cys27Ala)-A8B of human C5a

<400> SEQUENCE: 5 acgct gcaaaagaag atagaagaaa tagctgctaa atataaacat tcagtagtga         55
agaaatgttg ttacgatgga gccgccgtta ataatgatga aacctgtgag cagcgagctg    115
cacggattag tttagggcca agatgcatca aagctttcac cgaatgttgt gtcgtcgcaa    175
gccagctccg tgctaatatc tcttttaaaa ggtcgctgtt gtgc                     219

<210> SEQ ID NO 6
<211> LENGTH: 219
<212> TYPE: DNA
<213> ORGANISM: Artificial Sequence
<220> FEATURE:
<223> OTHER INFORMATION: mutant (C5a-(1-66, Cys27Ala)-A8B-Leu70Try73 of
      human C5a

<400> SEQUENCE: 6 acgctg caaaagaaga tagaagaaat agctgctaaa tataaacatt cagtagtgaa         56
gaaatgttgt tacgatggag ccgccgttaa taatgatgaa acctgtgagc agcgagctgc    116
acggattagt ttagggccaa gatgcatcaa agctttcacc gaatgttgtg tcgtcgcaag    176
ccagctccgt gctaatatct cttttaaaag gctgctgttg tat                      219

<210> SEQ ID NO 7
<211> LENGTH: 219
<212> TYPE: DNA
<213> ORGANISM: Artificial Sequence
<220> FEATURE:
<223> OTHER INFORMATION: mutant (C5a-(1-66,Cys27Ala)-A8B-Lys69Ala70 of
      human C5a

<400> SEQUENCE: 7 acgctgc aaaagaagat agaagaaata gctgctaaat ataaacattc agtagtgaag        57
aaatgttgtt acgatggagc cgccgttaat aatgatgaaa cctgtgagca gcgagctgca    117
cggattagtt tagggccaag atgcatcaaa gctttcaccg aatgttgtgt cgtcgcaagc    177
cagctccgtg ctaatatctc ttttaaaaag gcgctgttgc gt                       219

<210> SEQ ID NO 8
<211> LENGTH: 219
<212> TYPE: DNA
<213> ORGANISM: Artificial Sequence
<220> FEATURE:
<223> OTHER INFORMATION: mutant 1-66, Cys27Arg)-A8B of human C5a

<400> SEQUENCE: 8 acgctgca aaagaagata gaagaaatag ctgctaaata taaacattca gtagtgaaga       58
aatgttgtta cgatggagcc ccgcgttaata atgatgaaac ctgtgagcag cgagctgcac   118
ggattagttt agggccaaga tgcatcaaag ctttcaccga atgttgtgtc gtcgcaagcc    178
agctccgtgc taatatctct tttaaaaggt cgctgttgcg t                        219

<210> SEQ ID NO 9
<211> LENGTH: 210
<212> TYPE: DNA
<213> ORGANISM: Artificial Sequence
<220> FEATURE:
<223> OTHER INFORMATION: mutant (C5a-(1-66,Cys27Ala)-A8B-Del.71-73 of
``` human C5a

<400> SEQUENCE: 9

```
acgctgcaa aagaagatag aagaaatagc tgctaaatat aaacattcag tagtgaagaa      59
atgttgttac gatggagccg ccgttaataa tgatgaaacc tgtgagcagc gagctgcacg    119
gattagttta gggccaagat gcatcaaagc tttcaccgaa tgttgtgtcg tcgcaagcca    179
gctccgtgct aatatctctt ttaaaaggtc g                                   210
```

<210> SEQ ID NO 10
<211> LENGTH: 228
<212> TYPE: DNA
<213> ORGANISM: Artificial Sequence
<220> FEATURE:
<223> OTHER INFORMATION: mutant (C5a-(1-66, Gly -2, -1, Cys27Ala) A8B of human C5a

<400> SEQUENCE: 10

```
tgcggtggta cgctgcaaaa gaagatagaa gaaatagctg ctaaatataa acattcagta     60
gtgaagaaat gttgttacga tggagccgcc gttaataatg atgaaacctg tgagcagcga   120
gctgcacgga ttagtttagg gccaagatgc atcaaagctt tcaccgaatg ttgtgtcgtc   180
gcaagccagc tccgtgctaa tatctctttt aaaaggtcgc tgttgcgt                228
```

<210> SEQ ID NO 11
<211> LENGTH: 219
<212> TYPE: DNA
<213> ORGANISM: Artificial Sequence
<220> FEATURE:
<223> OTHER INFORMATION: mutant (C5a-(1-66, Cys27Arg)- A8B-Ala691 of human C5a

<400> SEQUENCE: 11

```
acgctgcaaa a gaagatagaa gaaatagctg ctaaatataa acattcagta              51
gtgaagaaat gttgttacga tggagccgcc gttaataatg atgaaacctg tgagcagcga   111
gctgcacgga ttagtttagg gccaagatgc atcaaagctt tcaccgaatg ttgtgtcgtc   171
gcaagccagc tccgtgctaa tatctctttt aaagcgtcgc tgttgcgt                219
```

<210> SEQ ID NO 12
<211> LENGTH: 219
<212> TYPE: DNA
<213> ORGANISM: Artificial Sequence
<220> FEATURE:
<223> OTHER INFORMATION: mutant (C5a-(1-66,Cys27Arg) -A8B-Asp69 of human C5a

<400> SEQUENCE: 12

```
acgctgcaaa ag aagatagaag aaatagctgc taaatataaa cattcagtag             52
tgaagaaatg ttgttacgat ggagccgccg ttaataatga tgaaacctgt gagcagcgag   112
ctgcacggat tagtttaggg ccaagatgca tcaaagcttt caccgaatgt tgtgtcgtcg   172
caagccagct ccgtgctaat atctctttta aagactcgct gttgcgt                 219
```

<210> SEQ ID NO 13
<211> LENGTH: 74
<212> TYPE: PRT
<213> ORGANISM: Homo Sapiens

<400> SEQUENCE: 13

Thr Leu Gln Lys Lys Ile Glu Glu Ile Ala Ala Lys Tyr Lys His Ser
1               5                   10                  15

```
Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 14
<211> LENGTH: 73
<212> TYPE: PRT
<213> ORGANISM: Artificial Sequence
<220> FEATURE:
<223> OTHER INFORMATION: mutant (C5a-(1-66,Cys27Ala)-A8B of human C5a

<400> SEQUENCE: 14

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser Leu Leu Arg
65                  70

<210> SEQ ID NO 15
<211> LENGTH: 73
<212> TYPE: PRT
<213> ORGANISM: Artificial Sequence
<220> FEATURE:
<223> OTHER INFORMATION: mutant (C5a-(1-66, Cys27Ala)-A8B-Leu70 of
      human C5a

<400> SEQUENCE: 15

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Leu Leu Leu Arg
65                  70

<210> SEQ ID NO 16
<211> LENGTH: 71
<212> TYPE: PRT
<213> ORGANISM: Artificial Sequence
<220> FEATURE:
<223> OTHER INFORMATION: mutant (C5a-(1-66,Cys27Ala)-A8B-Cys72 of
      human C5a

<400> SEQUENCE: 16

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30
```

```
Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser Cys
65                  70

<210> SEQ ID NO 17
<211> LENGTH: 73
<212> TYPE: PRT
<213> ORGANISM: Artificial Sequence
<220> FEATURE:
<223> OTHER INFORMATION: mutant  (C5a-(1-66,Cys27Ala)-A8B-Cys73 of
      human C5a

<400> SEQUENCE: 17

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser Leu Leu Cys
65                  70

<210> SEQ ID NO 18
<211> LENGTH: 73
<212> TYPE: PRT
<213> ORGANISM: Artificial Sequence
<220> FEATURE:
<223> OTHER INFORMATION: mutant (C5a-(1-66, Cys27Ala) -A8B-Leu70Tyr73 of
      human C5a

<400> SEQUENCE: 18

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Leu Leu Leu Tyr
65                  70

<210> SEQ ID NO 19
<211> LENGTH: 72
<212> TYPE: PRT
<213> ORGANISM: Artificial Sequence
<220> FEATURE:
<223> OTHER INFORMATION: mutant (C5a-(1-66, Cys27Ala) -A8B-Lys69Ala70 of
      human C5a

<400> SEQUENCE: 19

Thr Leu Gln Lys Lys Ile Glu Glu Ile Ala Ala Lys Tyr Lys His Ser
1               5                   10                  15

Val Val Lys Lys Cys Cys Tyr Asp Gly Ala Val Asn Asn Asp Glu Thr
            20                  25                  30

Cys Glu Gln Arg Ala Ala Arg Ile Ser Leu Gly Pro Arg Cys Ile Lys
        35                  40                  45
```

```
Ala Phe Thr Glu Cys Cys Val Val Ala Ser Gln Leu Arg Ala Asn Ile
    50                  55                  60

Ser Phe Lys Lys Ala Leu Leu Arg
65                  70

<210> SEQ ID NO 20
<211> LENGTH: 73
<212> TYPE: PRT
<213> ORGANISM: Artificial Sequence
<220> FEATURE:
<223> OTHER INFORMATION: mutant (C5a-(1-66, Cys27Arg)-A8B of human C5a

<400> SEQUENCE: 20

Thr Leu Gln Lys Lys Ile Glu Glu Ile Ala Ala Lys Tyr Lys His Ser
1               5                   10                  15

Val Val Lys Lys Cys Cys Tyr Asp Gly Ala Arg Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
    50                  55                  60

Ile Ser Phe Lys Arg Ser Leu Leu Arg
65                  70

<210> SEQ ID NO 21
<211> LENGTH: 70
<212> TYPE: PRT
<213> ORGANISM: Artificial Sequence
<220> FEATURE:
<223> OTHER INFORMATION: mutant (C5a-(1-66, Cys27Ala) -A8B-Del.71-73 of
      human C5a

<400> SEQUENCE: 21

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
    50                  55                  60

Ile Ser Phe Lys Arg Ser
65                  70

<210> SEQ ID NO 22
<211> LENGTH: 75
<212> TYPE: PRT
<213> ORGANISM: Artificial Sequence
<220> FEATURE:
<223> OTHER INFORMATION: mutant (C5a-(1-66, Gly-1,-2,Cys27Arg) -A8B of
      human C5a

<400> SEQUENCE: 22

Cys Gly Gly Thr Leu Gln Lys Lys Ile Glu Glu Ile Ala Ala Lys Tyr
1               5                   10                  15

Lys His Ser Val Val Lys Lys Cys Cys Tyr Asp Gly Ala Arg Val Asn
                20                  25                  30

Asn Asp Glu Thr Cys Glu Gln Arg Ala Arg Ile Ser Leu Gly Pro Arg
            35                  40                  45

Cys Ile Lys Ala Phe Thr Glu Cys Cys Val Val Ala Ser Gln Leu Arg
    50                  55                  60
```

Ala Asn Ile Ser Phe Lys Arg Ser Leu Leu Arg
65              70              75

<210> SEQ ID NO 23
<211> LENGTH: 73
<212> TYPE: PRT
<213> ORGANISM: Artificial Sequence
<220> FEATURE:
<223> OTHER INFORMATION: mutant (C5a-(1-66,Cys27Arg) -A8B-Ala69 of human
      C5a

<400> SEQUENCE: 23

Thr Leu Gln Lys Lys Ile Glu Glu Ile Ala Ala Lys Tyr Lys His Ser
1               5                   10                  15

Val Val Lys Lys Cys Cys Tyr Asp Gly Ala Arg Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Ala Ser Leu Leu Arg
65              70

<210> SEQ ID NO 24
<211> LENGTH: 73
<212> TYPE: PRT
<213> ORGANISM: Artificial Sequence
<220> FEATURE:
<223> OTHER INFORMATION: mutant (C5a-(1-66,Cys27Arg) -A8B-Asp69 of human
      C5a

<400> SEQUENCE: 24

Thr Leu Gln Lys Lys Ile Glu Glu Ile Ala Ala Lys Tyr Lys His Ser
1               5                   10                  15

Val Val Lys Lys Cys Cys Tyr Asp Gly Ala Arg Val Asn Asn Asp Glu
            20                  25                  30

Thr Cys Gly Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Asp Ser Leu Leu Arg
65              70

<210> SEQ ID NO 25
<211> LENGTH: 34
<212> TYPE: DNA
<213> ORGANISM: Artificial Sequence
<220> FEATURE:
<223> OTHER INFORMATION: Primer JK124

<400> SEQUENCE: 25
gagagagaga gagctcacgc tgcaaaagaa gata                              34

<210> SEQ ID NO 26
<211> LENGTH: 21
<212> TYPE: DNA
<213> ORGANISM: Artificial Sequence
<220> FEATURE:
<223> OTHER INFORMATION: Primer JK116

<400> SEQUENCE: 26
cgaattgggt accttattaa c                                            21

```
<210> SEQ ID NO 27
<211> LENGTH: 45
<212> TYPE: DNA
<213> ORGANISM: Artificial Sequence
<220> FEATURE:
<223> OTHER INFORMATION: Primer JK146

<400> SEQUENCE: 27
gagagagaga ggtaccttat taacgcaaca gcagcctttt aaaag            45

<210> SEQ ID NO 28
<211> LENGTH: 39
<212> TYPE: DNA
<213> ORGANISM: Artificial Sequence
<220> FEATURE:
<223> OTHER INFORMATION: Primer JK148

<400> SEQUENCE: 28
gagagagaga ggtaccttat taacacgacc ttttaaaag                   39

<210> SEQ ID NO 29
<211> LENGTH: 45
<212> TYPE: DNA
<213> ORGANISM: Artificial Sequence
<220> FEATURE:
<223> OTHER INFORMATION: Primer JK130

<400> SEQUENCE: 29
gagagagaga ggtaccttat tagcacaaca gcgacctttt aaaag            45

<210> SEQ ID NO 30
<211> LENGTH: 45
<212> TYPE: DNA
<213> ORGANISM: Artificial Sequence
<220> FEATURE:
<223> OTHER INFORMATION: Primer JK126

<400> SEQUENCE: 30
gagagagaga ggtaccttat taatacaaca gcagcctttt aaaag            45

<210> SEQ ID NO 31
<211> LENGTH: 45
<212> TYPE: DNA
<213> ORGANISM: Artificial Sequence
<220> FEATURE:
<223> OTHER INFORMATION: Primer JK147

<400> SEQUENCE: 31
gagagagaga ggtaccttat taacgcaaca gcgactttta aaaag            45

<210> SEQ ID NO 32
<211> LENGTH: 21
<212> TYPE: DNA
<213> ORGANISM: Artificial Sequence
<220> FEATURE:
<223> OTHER INFORMATION: Primer JK152

<400> SEQUENCE: 32
gagcccgcgt taataatgat g                                      21

<210> SEQ ID NO 33
<211> LENGTH: 25
<212> TYPE: DNA
<213> ORGANISM: Artificial Sequence
<220> FEATURE:
<223> OTHER INFORMATION: Primer JK153
```

-continued

```
<400> SEQUENCE: 33
catcgtaaca acatttcttc actac                                          25

<210> SEQ ID NO 34
<211> LENGTH: 36
<212> TYPE: DNA
<213> ORGANISM: Artificial Sequence
<220> FEATURE:
<223> OTHER INFORMATION: Primer JK149

<400> SEQUENCE: 34
gagagagaga ggtaccttat tacgaccttt taaaag                              36

<210> SEQ ID NO 35
<211> LENGTH: 45
<212> TYPE: DNA
<213> ORGANISM: Artificial Sequence
<220> FEATURE:
<223> OTHER INFORMATION: Primer JK154

<400> SEQUENCE: 35
gagagagaga ggtaccttat taacgcaaca gcgacgcttt aaaag                    45

<210> SEQ ID NO 36
<211> LENGTH: 47
<212> TYPE: DNA
<213> ORGANISM: Artificial Sequence
<220> FEATURE:
<223> OTHER INFORMATION: Primer 156

<400> SEQUENCE: 36
gagagagaga ggtaccttat taacgcaaca gcgagtctta aaaagag                  47

<210> SEQ ID NO 37
<211> LENGTH: 43
<212> TYPE: DNA
<213> ORGANISM: Artificial Sequence
<220> FEATURE:
<223> OTHER INFORMATION: Primer JK156

<400> SEQUENCE: 37
gagagagaga gagctctgcg gtggtacgct gcaaaagaag ata                      43

<210> SEQ ID NO 38
<211> LENGTH: 45
<212> TYPE: DNA
<213> ORGANISM: Artificial Sequence
<220> FEATURE:
<223> OTHER INFORMATION: Primer JK156

<400> SEQUENCE: 38
gagagagaga ggtaccttat taatacagca acaacagttt aaaag                    45

<210> SEQ ID NO 39
<211> LENGTH: 72
<212> TYPE: PRT
<213> ORGANISM: Artificial Sequence
<220> FEATURE:
<223> OTHER INFORMATION: mutant (C5a-(1-66,Cys27Ala)-A5a of human C5a

<400> SEQUENCE: 39

Thr Leu Gln Lys Lys Ile Glu Glu Ile Ala Ala Lys Tyr Lys His Ser
1               5                   10                  15

Val Val Lys Cys Cys Tyr Asp Gly Ala Arg Val Asn Asn Asp Glu Thr
            20                  25                  30
```

```
Cys Glu Gln Arg Ala Ala Arg Ile Ser Leu Gly Pro Arg Cys Ile Lys
         35                  40                  45

Ala Phe Thr Glu Cys Cys Val Val Ala Ser Gln Leu Arg Ala Asn Ile
     50                  55                  60

Ser Phe Lys Leu Leu Leu Arg
65                   70

<210> SEQ ID NO 40
<211> LENGTH: 219
<212> TYPE: DNA
<213> ORGANISM: Artificial Sequence
<220> FEATURE:
<223> OTHER INFORMATION: mutant (C5a-(1-66,Cys27Ala) -A5a of human C5a

<400> SEQUENCE: 40
acgctgcaaa agaagataga agaaatagct gctaaatata acattcagt agtgaagaaa       60 tgttgttacg atggagccgc cgttaataat gatgaaacct gtgagcagcg agctgcacgg     120
attagtttag ggccaagatg catcaaagct ttcaccgaat gttgtgtcgt cgcaagccag     180
ctccgtgcta atatctcttt taaactgttg ttgctgaga                            219

<210> SEQ ID NO 41
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 41

Phe Lys Arg Ser Leu Leu Arg
1               5

<210> SEQ ID NO 42
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 42

Phe Lys Arg Leu Leu Leu Arg
1               5

<210> SEQ ID NO 43
<211> LENGTH: 5
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 43

Phe Lys Arg Ser Cys
1               5

<210> SEQ ID NO 44
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 44
```

```
Phe Lys Arg Ser Leu Leu Cys
 1               5

<210> SEQ ID NO 45
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 45

Phe Lys Arg Leu Leu Leu Tyr
 1               5

<210> SEQ ID NO 46
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 46

Phe Lys Lys Ala Leu Leu Arg
 1               5

<210> SEQ ID NO 47
<211> LENGTH: 4
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 47

Phe Lys Arg Ser
 1

<210> SEQ ID NO 48
<211> LENGTH: 7
<212> TYPE: PRT
<213> ORGANISM: Artificial Sequence
<220> FEATURE:
<223> OTHER INFORMATION: C-terminal amino acid sequence of a C5a
      receptor antagonist

<400> SEQUENCE: 48

Phe Lys Leu Leu Leu Leu Arg
 1               5

<210> SEQ ID NO 49
<211> LENGTH: 11
<212> TYPE: PRT
<213> ORGANISM: Artificial Sequence
<220> FEATURE:
<223> OTHER INFORMATION: N-Terminal Linker Sequence

<400> SEQUENCE: 49

Cys Gly Gly Gly Gly Ser Gly Gly Gly Gly Ser
 1               5                  10
```

MUTEINS OF C5A ANAPHYLATOXIN AND METHODS OF INHIBITING C5A

The present invention refers to muteins (mutant proteins) of the C5a anaphylatoxin (C5a) which are C5a receptor antagonists and to nucleic acid molecules comprising a nucleotide sequence encoding such muteins of the C5a anaphylatoxin that are C5a receptor antagonists. The invention further refers to host cells containing a nucleic acid molecule comprising a nucleotide sequence encoding such muteins of the C5a anaphylatoxin as well as to a pharmaceutical composition comprising a mutein of the C5a anaphylatoxin acting as a C5a receptor antagonist. The invention also refers to the use of muteins of the C5a anaphylatoxin which are C5a receptor antagonists for the manufacture of a medicament, to a method of treating a C5a-mediated disease or inflammatory condition as well as to a method of producing a mutein of the anaphylatoxin C5a.

Inflammation is a localized, protective event, elicited by injury, which serves to destroy, dilute or wall off both injurious agents and the injured tissues. It involves a complex series of events, including dilation of arteries, capillaries and venules, with increased vascular permeability, increased blood flow, and exudation of fluids and plasma proteins. These processes are often rapidly followed by adhesion of leukocytes to the vascular endothelium, with subsequent influx of the cells into the surrounding tissue.

The complement system, a major immunological defense mechanism against foreign substances, has been shown to influence each of the factors that comprise the inflammatory response. In general, complement comprises a set of proteins that work to eliminate microorganisms and other antigens from tissues and blood, to clear immune complexes, and to support the B-cell response. This task is achieved either by complement components alone or in cooperation with antibodies or with cells that express complement receptors. More specifically, the system consists of about 30 plasma proteins, their corresponding cellular receptors and several membrane regulatory proteins (see e.g. [1]). Activation of the complement system by, for example, antigen-antibody complexes or bacterial surface structures, triggers an amplification cascade of proteolytic cleavage and protein assembly events of the complement components, which ultimately leads to the destruction and final elimination of the foreign body (see e.g. [2]).

Several biologically active peptides are generated by the activation of the complement system. C5a, a glycoprotein containing 74 amino acids (cf. SEQ ID NO. 1) and having a molecular mass of about 11,000 in the glycosylated form, is generated by the proteolytic cleavage of the N-terminal end of the α-chain of C5, the fifth component of complement, by the enzyme C5 convertase [3].

The biological properties of C5a extend across a multitude of cells and tissues involved in both acute and chronic inflammatory processes. It mediates a variety of pro-inflammatory effector functions such as the recruitment of polymorphonuclear neutrophils (PMN), and macrophages to inflammatory sites and the activation of these cells to release increased levels of cytokines, chemokines, lysosomal enzymes, products of the arachidonic acid metabolism and histamine (reviewed, e.g. in [4] and [5]). C5a is a pivotal stimulus to the attraction of PMNs to the site of inflammation. In addition, endothelial cells are stimulated with increase P-selectin [3].

Complement is beneficial when directed against an appropriate target such as invading microorganisms or tumor cells, but has clear pathogenic potential if activated inappropriately. For instance, the anaphylatoxins, e.g., C5a, have been implicated as causative or aggravating factors in the pathogenesis of several inflammatory diseases such as sepsis [6], exogen allergic asthma ([7]-[9]), adult respiratory distress syndrome and rheumatoid arthritis [cf., 10, 11]. In particular, the aberrant presence of C5a in tissue has been detected in patients afflicted with allergic asthma [12], rheumatoid arthritis, osteoarthritis, psoriasis and noncardiac pulmonary edema. C5a has been found to be a principal inflammatory mediator produced by complement activation by virtue of additional activities that include recruitment and stimulation of inflammatory leukocytes and augmentation of antibody production (see, e.g., [13]).

The fact that C5a appears very early in the inflammatory cascade makes this molecule an interesting target for therapy. Since C5a exerts its various functions by binding to a specific C5a receptor found in the membrane of several human cells such as neutrophils, eosinophils and monocyte-derived cells, mast cells as well as activated B-cells and T-cells. the design of C5a receptor antagonists for inhibiting C5a-mediated inflammatory disorders and conditions have attracted considerable attention.

The U.S. Patents [14] and [15] disclose C-terminal analogs of C5a anaphylatoxin such a decapeptide analogs which possess a backbone confirmation that is constrained at the C-terminus to a β-turn. The stabilized β-turn is used to confer an increase in potency of the peptide analogs and to improve selectivity with respect to certain biological responses associated with C5a. WO publication [16] describes cyclic peptidic antagonists of C5a. The cyclization serves to constrain the conformation of the peptide analogs.

U.S. Patent [17] as well as [18] disclose recombinant human C5a receptor antagonists which were obtained by modification of the C-terminus of C5a. These polypeptides have the natural amino acid sequence at sequence positions 1 to 70 of human C5a; except for the substitution of Met1 by Thr, Cys 27 by Ser and in one case, the replacement of His 67 by Phe. The antagonistic property of these polypeptides was achieved by replacement of Gln 71 with cysteine. A mutant protein termed C5aRAM, which comprises Cys at position 71 and in which residues 72 to 74 are deleted, was reported to be a C5a receptor antagonist with a $K_i$ of $8 \times 10^{-9}$ M under the experimental conditions used. Experimental data indicated that the C5aRAM mutein might be suitable as a pharmacological agent in disorders and diseases associated with the activation of the C5a receptor.

Two further polypeptides named C5a-[A5A] and C5a-[A8B] (the latter is also referred to as C5a-A8) which have a Cys27Ala replacement and modifications in the C-terminal region of the C5a molecule and which show an antagonistic C5a receptor activity were found during studies on the interaction of C5a anaphylatoxin with the C5a receptor ([19], [20], [21]). In these studies, phage display libraries were constructed in which positions 67 to 73 of the C5a amino acid sequence were randomly mutated. The mutated proteins were expressed and characterized as fusion proteins, using the heterodimer of the proteins Jun and Fos as fusion partner (see FIG. 1 of [21] Heller et al. for a schematic illustration of the C5a fusion proteins).

The A8B mutein was expressed in a control experiment during these investigations without the Jun/Fos-fusion partner but with an hexahistidine (His6)-tag at its N-terminus. Contrasting to the Jun/Fos-C5a-fusion protein, this A8B-His6 variant showed no antagonistic activity but possessed the same agonistic activity as the recombinant wild-type C5a molecule equipped with a His6-tag (Table 23, page 101 of [19]). Accordingly, the antagonistic property of the Jun/Fos-fusion proteins was attributed to the fusion partner, i.e. the Jun/Fos heterodimer. On the molecular basis, it was assumed that Arg 69 of the A8B mutant is interacting with Jun or Fos, in particular with at least one of the numerous glutamate residues of the leucine zipper of Fos which can act as an electrostatic acceptor for the positively charged side chain of Arg 69. This interaction between the C-terminal region of the C5a and the Jun/Fos-heterodimer was assumed to lead to a reduced or changed binding of the C-terminus of C5a to the C5a receptor (page 120, last paragraph of [19]). Accordingly, the mutein Jun/Fos-A8B of C5a, which exhibited an $ID_{50}$ value of 17.6 nM for binding to the C5a receptor and blocked the C5a effector functions to nearly 100%, was regarded as a potential and specific therapeutic agent for treatment of C5a mediated immune complex diseases ([19], ([21], [22]).

It is an object of the present invention to provide other molecules which are antagonists of the C5a receptor and are suitable for therapeutic applications in disorders mediated by C5a receptor activity. It is a further object of the invention to provide a pharmaceutical composition useful for treating a C5a-mediated disease or an inflammatory condition.

These problems are solved among others by a mutein and the pharmaceutical composition as defined in the independent claims.

Such a mutein of the C5a anaphylatoxin is a mutein that is a C5a receptor antagonist, wherein the amino acid residue naturally occurring at sequence position 69 is mutated.

In preferred embodiments the residue at sequence position 69 is replaced by a positively charged amino acid residue. In other preferred embodiments the residue at position 69 is replaced by a leucine.

Figure 4:
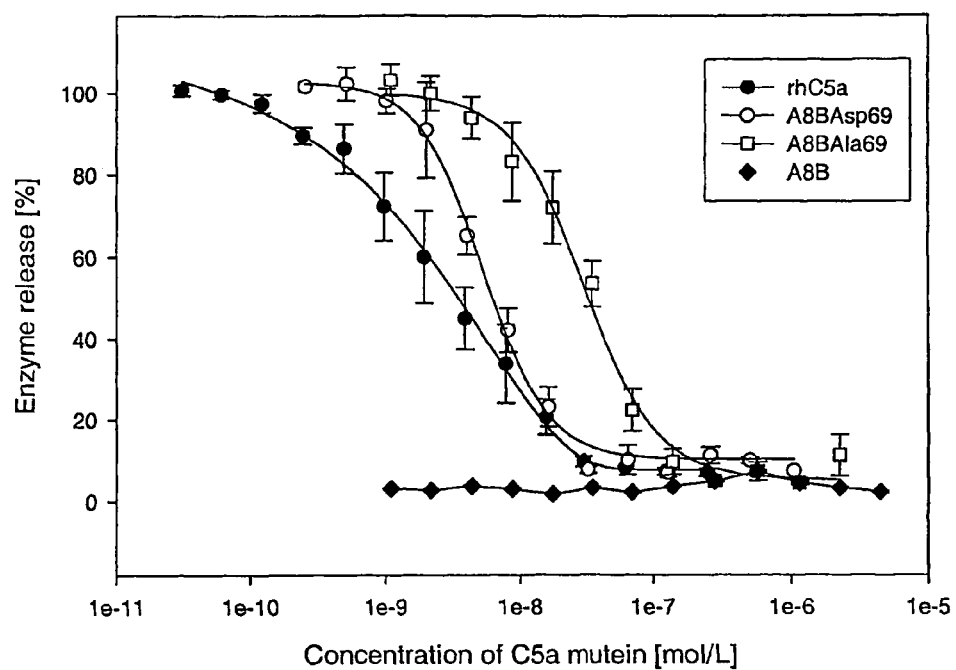

This means that the present invention is based on the surprising finding that the presence of a mutation (e.g., a positively charged amino acid residue) at sequence position 69 instead of the naturally present residue, which is Asp in the human C5a polypeptide, Asn in the bovine and porcine protein, Gly in the rat protein and Pro in the murine protein, contributes predominantly to the antagonistic property of the isolated mutant protein (cf. FIG. 4 and Table 1, showing that the substitution of Arg 69 by Asp in the mutein A8B-Asp69 or of Arg69 by Ala in the mutein A8B-Ala69 results in an agonistic activity of the polypeptide). This finding is particularly surprising, because so far there have not been any indications that sequence position 69 might be a receptor binding residue or somehow involved in the interaction of C5a with the C5a receptor. Rather, a contribution of sequence position 69 to the receptor interaction has been ruled out (see e.g. [23], [24], [25]).

In a preferred C5a mutein of the invention also the amino acid residue naturally occurring at sequence position 67 is mutated. In a further preferred embodiment, at least one of the amino acids residues at the sequence positions 67 and 70 to 74 of the natural amino acid sequence of C5a is mutated and/or at least one of the amino acid residues at the sequence positions 70 to 74 is deleted.

In accordance with the finding of the invention, the mutant C5a protein of the present invention comprises in one preferred embodiment at sequence positions 1 to 66 and 68 the natural amino acid sequence of the C5a anaphylatoxin.

However, it is also possible to introduce mutations at sequence positions 1 to 66 and 68 of the naturally occurring polypeptide sequence as long as those mutations do not interfere with the antagonistic receptor activity of the (isolated) C5a mutein. This includes that, for example, mutations such as substitutions, deletions and also insertions can be introduced into the natural amino acid sequence as long as the resulting polypeptide folds into a three-dimensionally stable structure.

Examples of possible alterations are conservatively modified variations where the alteration is the substitution of an amino acid with a chemically similar amino acid. Tables providing functionally similar amino acids are well known in the art. Examples of conservative substitutions are substitutions between: 1) alanine, serine, threonine; 2) aspartic acid and glutamic acid; 3) asparagine and glutamine; 4) arginine and lysine; 5) isoleucine, leucine, methionine, valin; and 6) phenylalanine, tyrosine, tryptophan.

It is, however, also possible to modify the sequence of the C5a muteins of the invention by non-conservative alterations. One example is the substitution of Met1 by Thr (cf. SEQ ID: 1 showing the amino acid sequence of rhC5a). A further example is the replacement of Cys27 by Arg (cf. SEQ ID NO: 20). Such modifications can also be used to further improve the antagonistic (inhibitory) potency of the muteins disclosed here. The mutein A8B Arg 27 (SEQ ID NO: 20), however, has the same inhibitory potency as the mutein A8B (SEQ ID NO: 14) which has a Cys27Ala replacement (see Table 1).

The sequence of a C5a mutein can also be modified for the purpose of improved stability, production, purification or applicability. For example, peptide segments which are not crucial for folding into a functional three-dimensional structure can be removed for these purposes, if wanted. Disulfide bonds can be eliminated by substitution of the cysteine residues or new disulfide bonds can be introduced at another site. Optionally, cysteine residues can also be newly introduced in order to prepare, for example, corresponding protein conjugates by chemical coupling with other components. Binding sites for further ligands, such as for example metal ions, can also be built into the C5a mutein.

The term "amino acid residue" as used herein refers to an amino acid either in the D or L form or to an amino acid mimetic that can be incorporated into a polypeptide by an amide bond. Accordingly, the positively charged amino acid residue at position 69 can for example either be a naturally occurring amino acid residue that is positively charged under physiological conditions such as arginine or lysine or a non-natural mimetic such as a lysine residue the α-amino group of which is alkylated in order to yield a (quarternary) ammonium-salt having a permanent positive charge.

By the term "antagonist", it is meant that the polypeptides disclosed here are inhibitors of C5a by interfering with the binding of C5a to the C5a receptor and that these polypeptides do not have an agonistic or anaphylatoxin activity (at all) or at least substantially no such agonistic or anaphylatoxin activity as defined below. The C5a muteins can be competitive inhibitors of C5a in that they compete with C5a for binding to the C5a receptor. However, the present invention is not limited to a specific molecular mechanism of inhibiting the C5a binding. The binding affinity to the C5a receptor, which is also referred to as "inhibitory potency" herein can be expressed by the $IC_{50}$ value obtained in a binding assay as described in [20] or as obtained in the competitive binding described in the experimental section of the present application. The $IC_{50}$ value represents the concentration of a mutein at which a half-maximal inhibitory activity occurs. A mutein of the invention shows in these assay an $IC_{50}$ value preferably of less than 1 μM, more preferably of less than 1 μm and most preferably of less than 10 nM when wild-type rC5a is used in a concentration of 1 nM.

The antagonistic (functional) activity or antagonism of the instant C5a muteins, for which binding to the C5a receptor as defined above is a prerequisite, can be quantified by various methods which are described in [20] or [21].

A preferred method for quantification of the antagonistic activity is the degranulation assay using dibutyryl cAMP induced U937 cells described in [23] or the Rat Basophil Leukemia (RBL) cell line 2H3 stably transfected with the human C5a receptor (C5aR-RBL) as described in [25]. The $ID_{50}$ value obtained in this assay is the concentration of a C5a mutant polypeptide inhibiting 50% of the N-acetyl-β-D-glucosaminidase release induced by a concentration of $1 \times 10^{-9}$ M of recombinant human C5a. The $ID_{50}$ values of the different C5a muteins are depicted in Table 1. The antagonistic muteins of the present invention preferably do not induce degranulation when used in concentrations as high as $4 \times 10^{-6}$ M.

The antagonistic potency may also be quantified as an $ID_{50}$ in the calcium rise assay described in [26]. This $ID_{50}$ value is defined as the concentration of a C5a mutein which inhibits 50% of the intracellular mobilization of calcium ions by PMNs bearing the C5a receptor, after a challenge dose with $1 \times 10^{-10}$ M or $1 \times 10^{-9}$ M human C5a (see also [17] and [21]).

A mutein of the present invention having antagonistic receptor activity is a polypeptide that has no or at least substantially no agonistic or anaphylatoxin activity. By the term "no anaphylatoxin activity" or "substantially no agonist activity," it is meant that the binding of the C5a mutein (to which is also interchangeably referred to as C5a receptor antagonist (C5aRA)) to the receptor does not cause one or more of the C5a effector functions at all or causes only minimal degree of one or more effector functions, which are insignificant in vitro or in vivo. This means, the binding to the C5a receptor does not result in an endogenous signal transduction event ultimately resulting in the physiological responses commonly associated with anaphylatoxin-induced inflammation caused by binding of C5a to its receptor, such as C5a-induced changes in intracellular $Ca^{2+}$ concentrations, activation of phagocytic cells, smooth muscle contraction, increase in vascular permeability, and excessive production of inflammatory mediators, e.g., histamines, prostaglandins, thromboxanes, leukotrienes, interleukins (IL) such as IL-1, IL-6 or IL-8 (see, e.g. [4] or [5]). A quantitative measure of the antagonistic property may be obtained using the degranulation assay described by Köhl [23] and below, or the calcium rise assay of [26].

The mutein of the present invention can be derived from the natural C5a sequence of mammal and non-mammal species. It can, for instance be of human, porcine, murine, bovine or rat origin. In a preferred embodiment, the mutein is a mutant protein of the human C5a protein.

In a preferred embodiment, the positively charged amino acid residue at sequence position 69 of the C5a mutein is Arg or Lys.

In a further preferred embodiment of the invention the mutein comprises a hydrophobic amino acid residue at sequence position 67. The aromatic hydrophobic amino acids Trp, Phe and Tyr are particularly preferred as residues at sequence position 67.

Also preferred antagonists are muteins which comprise a hydrophobic amino acid residue at one or more of the sequence positions 70, 71 or 72. Such hydrophobic amino acid residues can be selected independently from each other, they can be identical or different. Preferred hydrophobic residues are Leu, Ile and Ala.

Such muteins preferably comprise at sequence position 70 an amino acid residue which is selected from Ala or Leu. Other preferred muteins comprises Ser at sequence position 70.

A preferred amino acid at sequence position 71 is Leu. The antagonistic mutein disclosed can also preferably comprise a Leu residue at sequence position 72.

In a particularly preferred embodiment, the mutein comprises Leu at all of the sequence positions 70, 71, and 72.

If present, i.e. not deleted, in the C5a mutant, the sequence position 73 is preferably occupied by a Cys, Tyr, Arg or Ser residue. In preferred embodiments the mutein has a length of 70, 71, 72 or 73 amino acid residues. In general, Arg, Cys, Tyr or Ser are also preferred as C-terminal amino acid residues of a truncated mutein, i.e. a mutein having 70, 71, 72, or 73 amino acid residues. An example of an mutein having a length of 70 amino acids is the mutein C5a-(1-66, Cys27Ala)-FKRS-70 (cf. Table 1, SEQ ID NO: 18).

Further, muteins are also within the scope of the invention in which the positively charged amino acid at position 69 is the C-terminal (last) residue. Accordingly, such muteins can have a length of 69 amino acids. However, it is also possible to introduce deletions, for example, into the N-terminal region of the protein so that an antagonistic protein of the invention can comprises less than 69 amino acid residues. For clarity reasons it is noted once again that such deletions can, of course, also be present in muteins of the invention in which residues at sequence positions 70 to 74 are not or only partly deleted.

The mutein of the invention preferably comprises or has as C-terminal sequence a sequence selected from the group consisting of 67-FKRSLLR-73 (SEQ ID NO: 41) (cf. mutein A8B; SEQ ID NO: 14), 67-FKRLLLR-73 (SEQ ID NO: 42) (cf. mutein A8B-Leu-70; SEQ ID NO: 15), 67-FKRSC-71 (SEQ ID NO: 43) (cf. mutein Ab8-Cys71, SEQ ID NO: 16), 67-FKRSLLC-73 (SEQ ID NO: 44) (cf. mutein Ab8-Cys73, SEQ ID NO: 17), 67-FKRLLLY-73 (SEQ ID NO: 45) (cf. mutein A8B-Leu70-Tyr73, SEQ ID NO: 18), 67-FKKALLR-73 (SEQ ID NO: 46) (cf. mutein A8B-Lys69Ala70; SEQ ID NO: 19), 67-FKRS-70 (SEQ ID NO: 47) (cf. A8B-Del.71-73, SEQ ID NO: 21) and 67-FKLLLLY-73 (SEQ ID NO: 48) (cf. A5a, SEQ ID NO: 39). For the sake of clarity, the numbering refers to the amino acid position of C5a, i.e. 67-F means that phenylalanine is present as amino acid at sequence position 67 (see also Table 1).

The mutein can further comprise an Arg residue at sequence position 27, see, for example, mutein C5a-(1-66, Cys27Arg)-FKRSLLR (A8B-Arg27, SEQ ID NO: 20). In fact, Arg at position 27 is found in porcine and bovine C5a. In addition, muteins of human C5a with a Cys27Arg replacement were selected from C5a mutant phage library [27]. Muteins of C5a with only a Cys27Arg replacement are agonists of the C5a receptor [27].

Particularly preferred is a mutein of the human C5a anaphylatoxin having or comprising the amino acid sequence of SEQ ID NO: 14, i.e. C5a-(1-66, Cys27Ala-)A8B; SEQ ID NO: 15, i.e. C5a-(1-66, Cys27Ala)-A8B-Leu 70, SEQ ID NO: 16, i.e. C5a-(1-66, Cys27Ala)-Ab8-Cys71; SEQ ID NO: 17, i.e. C5a-(1-66, Cys27Ala)-A8B-Cys73; SEQ ID NO: 18; i.e. C5a-(1-66, Cys27Ala)-A8B-Leu70-Tyr73); SEQ ID NO: 19, i.e. C5a-(1-66, Cys27Ala)-A8B-Lys69-Ala70); SEQ ID NO: 20; i.e. C5a-(1-66, Cys27Arg)-A8B; SEQ ID NO: 21, i.e. C5a-(1-66, Cys27Ala)-A8B-Del.71-73), SEQ ID NO: 22, i.e. C5a-(1-66, Cys-3, Gly-2, -1, Cys27Ala)-A8B, and SEQ ID NO: 39, i.e. C5a-(1-66, Cys27Ala)A5a.

A mutant C5a antagonist of the present invention cannot only be present as the isolated (recombinant) protein but it can also be modified. In one embodiment, a mutein of the invention can be dimerized either with the same or a different mutein to form a homo- or heterodimer. For this purpose the mutein can comprise a N-terminal linker sequence which is capable of dimerizing the C5a mutein. One example of a preferred linker sequence linked to the N-terminus comprises the sequence Cys-Gly-Gly which can be used for spontaneous dimerization of the C5a mutein A8B in the course of the recombinant production of the mutant protein (cf. the mutein C5a-(1-66; Cys-3, Gly-2, -1; Cys27A1a)-A8B). Another example of such a suitable linker is Cys-(Gly-Gly-Gly-Gly-Ser)$_2$ (SEQ ID NO:49).

If the mutein carries a cysteine as C-terminal residue (cf. the muteins A8B-Cys71 and A8B-Cys73), the dimerization can also occur by coupling of two muteins via these C-terminal cysteine residues as described by [18]. The dimerization can also be achieved by linking a nucleotide sequence encoding a mutein in an appropriate reading frame with the nucleotide sequence coding for a protein which forms a homodimer in its native fold. Subsequent expression of the nucleic acid molecule yields a fusion protein consisting of the dimerization module linked to the C5a mutant polypeptide, which then dimerizes spontaneously. Examples of such proteins which can be used as dimerization modules are alkaline phosphatase, superoxide-dismutase or glutathione-S-transferase. The use these proteins is in particular useful because the respective functional fusion protein can readily be obtained by periplasmic expression in bacterial expression systems such as E. coli. The use of dimerization modules such as alkaline phosphatase or superoxide-dismutase provides the further advantage that such a fusion protein can easily be detected using a chromogenic reaction which is catalyzed e.g. by alkaline phosphatase. Suitable chromogenic substrates for these enzymes such as 5-bromo4-chloro-3-indolylphosphate for alkaline phosphatase are well known to the person skilled in the art. Those fusion proteins are therefore suitable as diagnostic reagents.

In accordance with the disclosure of the above paragraph, the mutein of the invention is in a further embodiment linked to a protein or a peptide tag, i.e. in which a fusion protein containing the C5a mutein is also part of the invention. However, the fusion proteins of the mutein A8B with Jun/Fos alone, and, with Jun/Fos and the minor coat protein (pIII) of the filamentous M13 phage fused to the N-terminus of the mutein A8B, which are known from [21] are excluded from the invention. The same applies to the mutein A8B that has a hexahistidine tag directly fused to the N-terminus, because this polypeptide is known from [19] and more importantly, it is an agonist and not an antagonist of the C5a receptor.

A fusion protein of the invention can comprise any suitable fusion partner, e.g., alkaline phosphatase or the green fluorescent protein (GFP) as long as the fusion partner does not interfere with the antagonistic properties of the mutein disclosed here and converts the mutein into an agonist when given to a patient, for example. A fusion partner appropriate for therapeutic purpose is a protein such as albumin which can enhance the in vivo (circulation) half-life of a mutein of the invention. The fusion partner can be fused to the N-terminus of the C5a mutein. Likewise, any peptide tag can be fused to the N-terminus of the mutein as long as its antagonistic property is maintained. Examples of suitable affinity tags are the Strep-tag® which has specific binding affinity for streptavidin or mutants thereof as Strep-Tactin® (see U.S. Patents [28] and [29]), the Flag®-tag or the myc-tag, all of which can be used for purification of the mutein by affinity chromatography.

It should, however, be noted that in the event of, e.g. inventive C5a muteins conjugated or fused to a partner that confers agonistic properties, the antagonistic muteins can be readily generated/released from its (fusion) partner by treatment such as limited proteolysis or cleavage, for example enzymatic or chemical cleavage, of a (peptide) bond which links the C5a mutein to the (fusion) partner. Accordingly, it is also within the scope of the present invention, to use a fusion partner, for example, for improved purification of the mutein, for example, even if this fusion partner confers an agonistic activity as long as this activity can be eliminated before (and thus the antagonistic activity of the inventive mutein is generated) the muteins is used, for instance, in a desired therapeutic application. It is also possible to use a mutein the antagonistic activity of which is reduced by the (fusion) partner but not completely abolished. In this case, it is thus not necessary to deliberate the mutein of the invention by cleavage from its (fusion) partner. Rather, the fusion protein or the conjugate as explained in the following can be used in a desired application.

The mutein of the present invention can also be conjugated to a protein or a different chemical (macromolecular) moiety via a suitable peptidic or non-peptidic linker that can be attached to any suitable residue within the primary sequence of the mutein. A protein can, for instance, be conjugated with the C5a mutein using solvent exposed α-amino groups of lysine residues and glutaraldehyde as linker. Another suitable coupling chemistry is amine-amine crosslinking using bis (succinimidylesters) of 5,5'-dithiobis-(2-nitrobenzoic acid) (DTNB) as described in [30] on page 96. Any protein can be coupled to the C5a mutein, depending on the desired application. For example, a conjugate with streptavidin, horseradish peroxidase or green fluorescent protein might be used as a diagnostic reagent or research tool for visualizing a C5a receptor on the surface or within different compartments of a cell.

In a preferred embodiment a mutein of the invention is conjugated to a moiety which enhances the in vivo half-life of the mutein. Such a conjugate is particularly useful when a present C5a antagonist is used for the treatment of chronic inflammatory disorders such as rheumatoid arthritis, lupus erythematosus, chronic hepatitis or psoriasis where a long term presence of the antagonist at the site of inflammation is desired. Suitable moieties are proteins such as human serum albumin. It is also possible to use a non-protein (macromolecular) moiety such as polyethylene glycol.

The C5a muteins including conjugates or fusion proteins thereof are useful in the treatment and/or prevention or prophylaxis of a variety of injurious conditions or diseases in which the complement system, and more particularly C5a and the C5a receptor, are involved. They are therapeutically very suitable when administered to any mammal such as cats, dogs, monkeys, rabbits, mice, rats and, of course, especially humans that face a high risk of C5a-mediated tissue destruction and death. In general, the conditions or diseases are usually those such as inflammatory disorders where C5a is generated proteolytically in serum or tissue.

Accordingly, the present invention also relates to a method of treating a C5a-mediated disease or inflammatory condition in a mammal which comprises the step of administering a pharmaceutical composition comprising an isolated or modified mutein alone or in combination with other pharmaceutically active agents and a pharmaceutically acceptable carrier to a mammal in need thereof.

Examples of diseases or inflammatory conditions or disorders which can be treated with a mutein described here include asthma, pneumonitis, adult respiratory distress syndrome (ARDS), idiopathic pulmonary fibrosis, pulmonary inflammation or injury, chronic progressive pulmonary discystic fibrosis, byssinosis, asbestos-induced inflammation, myocardial infarction, post-myocardial infarction inflammation, ischemic heart damage, ischeria/reperfusion (I/R) injury, I/R-induced local and remote injury such as hemmorrhage, inflammatory bowel disease (bowel wall edema), hepatic cirrhosis, primary biliary cirrhosis inflammation, chronic hepatitis, pancreatitis, hemorrhagic pancreatitis, colitis, ischernic brain damage, encephalitis, cranial nerve damage in meningitis, meningitis, uveitis, Purtscher's retinopathy, immune complex-mediated glomerulonephritis, Goodpasture's syndrome, renal cortical necrosis, gout, vasculitis, serum sickness, angio-edema, myasthenia gravis, systemic lupus erythematosus, rheumatoid arthritis, bullous skin disease, hypersensitivity, psoriasis, endotoxin shock, sepsis, severe trauma and burns.

The C5a muteins of the invention can also be used as therapeutic reagents to treat patients suffering from transplant rejection, patients receiving immunosuppressive therapy or massive blood transfusion, patients exposed to medical devices, and patients experiencing pulmonary dysfunction following hemodialysis and leukopheresis.

The C5a antagonists disclosed here can further be employed as a prophylactic agent, particularly in conditions caused by reperfusion, e.g., reperfusion following ischemia, and circulatory contact with medical devices, as well as to prevent transplant rejection. In this case, the C5a antagonist is administered suitably prior to or simultaneously with the event that is known to cause the inflammation or aggravate an existing inflammatory condition.

The C5a muteins of the invention can be administered by any therapeutically effective route for a proteinaceous drug, for instance, topically, parenterally, intranasally, rectally or buccally, in dosage unit formulations containing conventional non-toxic pharmaceutically acceptable carriers, adjuvants and vehicles as desired. The term "parenteral" comprises delivery modes such as subcutaneous, intravenous, intramuscular, instrasternal, intra-arterial injection and infusion techniques.

Dosage amounts of the C5a muteins of the present invention may be varied to achieve the desired therapeutic response for a particular patient. They will depend, for instance, on the activity of the particular antagonist, the mode of administration, the severity of the condition being treated, as well as the medical condition of the patient.

For example, for the treatment of an acute short term disorder such as septic shock, an asthmatic attack or ischemia/reperfusion injury, a dosis as high as possible is required. Contrasting, for treatment of chronic disorders such as rheumatoid arthritis, or psoriasis a lower dosage, given in a sustained release formulation might be more suitable. The determination of a therapeutically effective dosage amount for a given condition and patient is within the level of skill in the art.

In general, treatment dosage levels from about 500 µg to 50 mg per kilogram of body weight per day are administered daily to the mammalian host. Preferred dosage levels range from about 500 µg/kg to about 5 mg/kg of body weight per day for long term treatment and from 5 mg/kg to 50 mg/kg in short term treatments. The C5a mutein can be administered to the patient as a single continuous dose over a prolonged period of time. However, the total effective dosage may be divided into multiple doses, e.g., two to four separate doses per day, if desired.

Therefore, the invention is also directed to a pharmaceutical composition comprising a mutein as described above and a pharmaceutically acceptable carrier.

The C5a analogs of the present invention can be formulated into compositions using both known pharmaceutically acceptable ingredients and methods of preparation (see, e.g., [31]). Suitable compositions for parenteral administration comprise pharmaceutically acceptable sterile aqueous or non aqueous solutions, dispersions, suspensions or emulsions, as well as sterile powders for reconstitution into sterile injectable solutions or dispersions immediately prior to use. Representative examples of suitable aqueous and non-aqueous carriers, diluents, solvents or vehicles include water, ethanol, polyols, e.g., glycerol, propylene glycol, polyethylene glycol, and suitable mixtures thereof, vegetable oils, e.g., olive oil, and injectable organic esters such as ethyl oleate. Fluidity may be maintained by various means including the use of coating materials such as lecithin, the maintenance of required particle size (in the case of dispersions) and surfactants.

The pharmaceutical composition can also be adapted for topical administration, in particular for direct application onto the skin of a mammal patient. For this purpose, the pharmaceutical composition of the invention can be in the form of ointments, creams or tinctures. The way of administration is particularly suitable for treatment of conditions such as skin irritations caused by allergic reactions such as contact allergies to metal-ions, such as nickel-ions, or contact allergies to compounds such as Latex, poison ivy, poison oak, solvents, phosphate esters used in cosmetics or to diseases such as psoriasis. A composition for topical application may be based on conventional oil in water formulations of ointments. A suitable composition may, however, also be based on a oily basis such as vegetable oil, e.g. olive oil, in which a mutein of the invention is dissolved.

The compositions may also contain adjuvants such as preservatives, wetting agents, emulsifying agents, dispersing agents, antibacterial and antifungal agents such as paraben, chlorobutanol, phenol and sorbic acid, isotonic agents such as sugars, sodium chloride, or agents which delay absorption such as aluminum monostearate and gelatin. The C5a receptor antagonists may be incorporated into slow or sustained release or targeted delivery systems such as polymer matrices, liposomes and microspheres.

Injectable formulations can be sterilized by numerous means, including filtration through a bacteria-retaining filter, or by incorporating sterilizing agents in the form of sterile solid compositions which can be dissolved or dispersed in sterile water or other sterile injectable medium just prior to use.

In addition to the C5a mutein and optionally any other active ingredient, a pharmaceutical composition may contain suspending agents such as ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are usually in the form of suppositories which can be prepared by mixing the polypeptides of the present invention with suitable non-irritating excipients or carriers such as cocoa butter, polyethylene glycol or a suppository wax which is solid at room temperature but liquid at body temperature, and therefore melts in the rectum or vaginal cavity, and releases the mutein of the invention.

Finally, the pharmaceutical composition of the invention can also be in the form of opthalmic formulations, eye ointments, powders and solutions.

In addition, the invention is also directed to a nucleic acid molecule comprising a nucleotide sequence encoding a mutein of the C5a anaphylatoxin disclosed herein. In preferred embodiments the nucleic acid molecule comprises a nucleotide sequence encoding a C5a mutein of SEQ ID NO: 14, SEQ ID NO: 15, SEQ ID NO: 16, SEQ ID NO: 17, SEQ ID NO: 18, SEQ IQ NO: 19, SEQ ID NO: 20, SEQ ID NO: 21, SEQ ID NO: 22 or SEQ ID NO:39. Since the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for a functional C5a antagonist of the present invention.

In a preferred embodiment the nucleic acid molecule comprises a nucleotide sequence selected from the group consisting of SEQ ID. NO: 2 to SEQ ID NO: 11 and SEQ ID NO: 40.

The nucleic acid molecule disclosed here that comprises a nucleotide sequence encoding a C5a mutein can be operably linked to a regulatory sequence to allow expression of the nucleic acid molecule.

A nucleic acid molecule such as DNA is regarded to be "capable of expressing a nucleic acid molecule or a coding nucleotide sequence" or capable "to allow expression of a nucleotide sequence" if it contains regulatory nucleotide sequences which contain transcriptional and translational information and such sequences are "operably linked" to nucleotide sequences which encode the polypeptide. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of the synthesis. Such regions will normally include non-coding regions which are located 5' and 3' to the nucleotide sequence to be expressed and which are involved with initiation of transcription and translation such as the TATA box, capping sequence, CAAT sequences. These regions can, e.g., also contain enhancer sequences or translated signal and leader sequences for targeting the produced polypeptide to a specific compartment of a host cell, which is used for producing a recombinant mutein of the present invention.

Accordingly, a nucleic acid of the invention can comprise a regulatory sequence, preferably a promoter sequence. In another embodiment, a nucleic acid of the invention comprises a transcriptional initiating region functional in a cell and a transcriptional terminating region functional in a cell. Suitable promoter sequence that can be used in the invention are, e.g., the lac promoter, the tet-promoter or the T7 promoter in the case of bacterial expression. An example of a promoter suitable for expression in eukaryotic systems is the SV 40 promoter.

In a further preferred embodiment, the nucleic acid molecule is comprised in a vector, in particular in an expression vector. Such an expression vector can comprise, besides the above-mentioned regulatory sequences and a nucleic acid sequence which codes for a nucleic acid sequence coding for the mutein in 5' or/and 3' direction. This vector also allows the introduction of another nucleic acid sequence coding for a protein to be expressed or a protein part. The expression vector preferably also contains replication sites and control sequences derived from a species compatible with the host that is used for expression. The expression vector can be based on well known plasmids such as pBR322, puC19, pBluescript and the like.

The DNA molecules encoding the C5a muteins and in particular a vector containing the coding sequence of a mutein can be transformed into host cells capable of expressing the genes. The transformation can be carried out in accordance with standard techniques. Thus, the invention is also directed to a (recombinant) host cell containing a nucleic acid molecule as defined above.

The transformed host cells are cultured under conditions suitable for expression of the nucleotide sequence encoding a C5a mutein disclosed here. Representative host cells include prokaryotes such as *E. coli, Bacillus* such as *B. subtilis; Streptomyces, Salmonella*, and eukaryotes such as filamentous fungi, e.g., *Aspergillus niger*; yeast, e.g., *Saccharomyces cerevisiae, Pichia pastoris* and *Yarrowia lipolytica*; insect cells such as (SF9) cells infected with baculovirus or mammalian cells such as Hela cells or CHO cells or tissue culture. Suitable prokaryotic, eukaryotic and mammalian expression systems are reviewed in [32] to [35].

Finally, the invention also relates to a method of producing a mutein having antagonistic C5a receptor activity. This method comprises the steps of (a) introducing into a nucleic acid molecule encoding the C5a anaphylatoxin polypeptide a nucleotide sequence mutating the residue at sequence position 69 of the C5a polypeptide, and (b) introducing the obtained nucleic acid molecule for expression into a suitable host cell or into a suitable cell extract or cell lysate.

Preferably, a nucleotide sequence (a codon) encoding leucine or a positively charged amino acid residue is introduced at sequence position 69 of the C5a polypeptide.

The method further comprises in preferred embodiments mutating the nucleotide sequence encoding sequence position 67 and/or deleting the nucleotide sequence encoding sequence positions 70 to 74 of the natural amino acid sequence of the C5a polypeptide.

The modification of step (a) can either be performed with a nucleic acid coding only for the C5a polypeptide or with a nucleic acid molecule such as an expression vector, in which the C5a coding sequence is operably linked to regulatory sequences and optionally fused to the sequence coding for a fusion partner such as an affinity tag or another protein. The latter approach is preferred since it avoids the need of a further cloning step. The expression of the mutated gene can be carried out in vivo using a recombinant cell such as *E. coli* or insect cells such as SF 9 cells. Alternatively, the expression can also be achieved in vitro by use of a suitable cell extract or cell lysate which contains all factors and components necessary for in vitro transcription of a DNA molecule and/or translation of the corresponding RNA into the polypeptide.

For recombinant production of a C5a antagonist of the invention, it is preferred to direct the polypeptide into a cell compartment having an oxidizing thiol/disulfide redox milieu by use of a suitable signal sequence. Such an oxidizing milieu is present in the periplasm of bacteria such as *E. coli* or in the lumen of the endoplasm reticulum of a eukaryotic cell. It is, however, also possible to produce a polypeptide of the invention in the cytosol of a host cell, preferably *E. coli*. In this case the polypeptide can, for instance, be produced in form of inclusion bodies, followed by renaturation in vitro (cf. e.g. [18] or [23]). A further option is the use of specifically mutated strains which have an oxidizing milieu in the cytosol and thus allow production of the native protein in the cytosol. If *E. coli* is used as host for expression, a preferred signal sequence for transport of the polypeptide into the periplasm is the pelB signal sequence.

The invention is further illustrated by the following non-limiting Examples, Tables and Figures.

FIG. 1 shows the amino acid sequence and the nucleotide sequence of recombinant C5a as published in [36]. The nucleotide sequence of C5a corresponds to that of SEQ ID NO: 1.

FIG. 2 shows a typical SDS-PAGE of eluted fractions of a C5a mutein after immune affinity chromatography using anti-C5a specific mAb 561. The purified protein was loaded in lanes 1 and 2. The proteins were visualized by silver staining. M denotes the marker proteins used as molecular weight marker.

FIG. 3 shows competitive binding studies of rhC5a and C5a muteins which are C5a receptor antagonists using RBL-cells stably transfected with the human C5a receptor [25]. The $IC_{50}$, of the C5a muteins are 8 (C5a-(1-66)-Cys27Ala-A8B-Leu70-Tyr73) to 16 fold (C5a-(1-67)-Cys27Arg-A8B) lower as compared to recombinant human C5a (rhC5a); (see also Table 1). The values for rhC5a ("isolated" curve closest to the y-axis) are depicted as black circles, those for the mutein A8B as rhombi, for A8BLeu70 as triangles, for A8BLeu70Tyr73 as squares, for A8BArg as hexagons, for A8Bdel71-73 as dark-gray circles and those for A8BCys73 as light-gray circles.

FIG. 4 shows the results of a degranulation assay using rhC5a (full circles), using the mutein C5aRA A8B (rhombi) and using muteins of the C5aRA A8B with either an Arg69Ala (C5a-(1-66)-Cys27Ala-A8B-Ala69) (open squares) or an Arg69Asp (C5a-(1-66)-Cys27Ala-A8B-Asp69) (open circles) replacement. The muteins A8B-Arg69Ala and A8B-Arg69Asp induce degranulation similar to C5a. In fact, the mutation switches the antagonistic function of the C5a mutein A8B towards an agonistic function, showing the contribution of the positively charged residue at position 69 to the antagonistic properties of the muteins of the invention.

Figure 5:
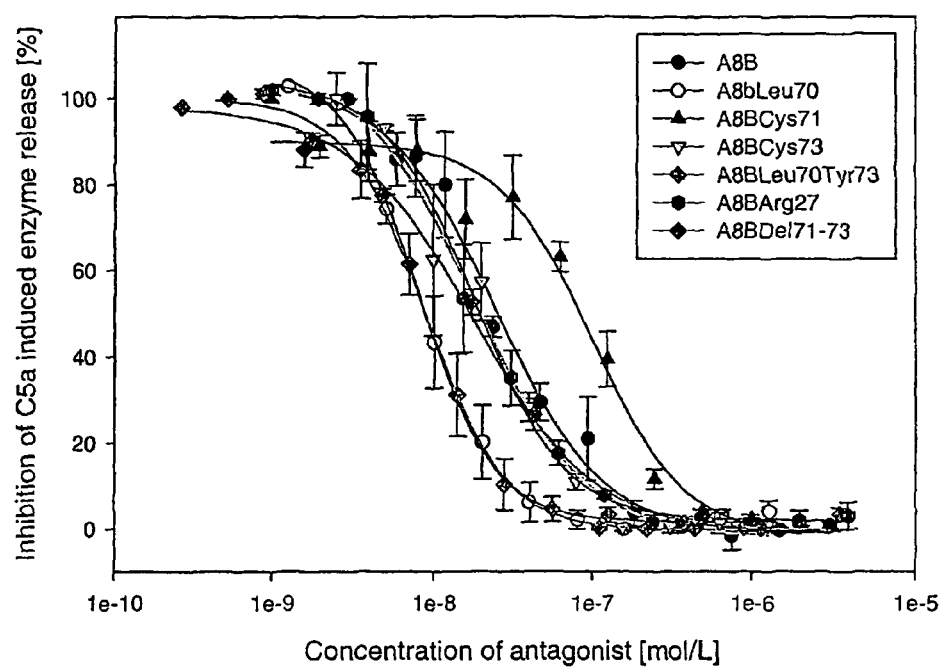

FIG. 5 depicts the inhibitory potency of C5a muteins (SEQ ID NOs: 14-18, 20, 21) of the invention. Increasing concentration of the different C5a muteins were used to inhibit the enzyme release from C5aR-RBL cells induced by a stimulus of $10^{-9}$ M rhC5a. The $ID_{50s}$ range from $7.9\times10^{-9}$ M (C5a-(1-66, Cys27Ala)-A8B-Leu70 to $99.2\times10^{-9}$M (C5a-(1-66, Cys27Ala)-A8B-Cys71). The values for the mutein A8B are depicted as black circles, those for A8BLeu70 as open circles, for A8Bcys71 as upward pointing triangles, for A8B Cys73 as downward pointing triangles, A8BLeu70Tyr73 as rhombi, for A8BArg27 as hexagons, and for A8Bdel71-73 as dark-gray rhombi.

Figure 6:
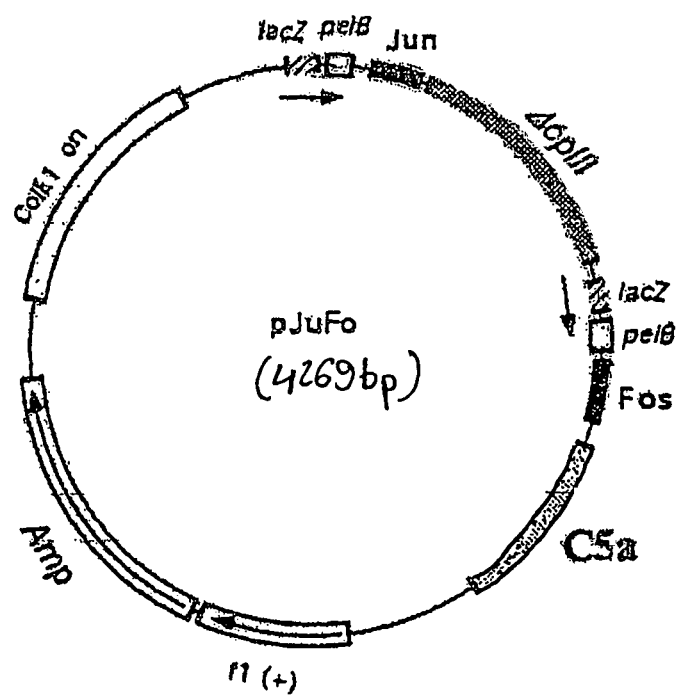

FIG. 6 shows a schematic representation of the vector pJuFo (4269 bp, [37]) on which the expression vector (pΔ-JuFo ΔpIII-A8B=pA8B) is based that was used for expression of the muteins of the invention. As explained in the Examples, the structural gene of the C5a muteins are equipped with the bacterial signal sequence of pelb and are arranged under the transcriptional control of the lacZ promoter/operator. As explained in [37], the vector pJuFo is derived from the vector pComb which is described in [38].

Table 1 summarizes the binding and functional properties of preferred C5a mutants of the invention compared to rC5a. Table 1 also depicts the differences in the amino acid sequence of these preferred muteins compared to rC5a. $IC_{50}$ values in Table 1 represent the half-maximal inhibitory concentrations ($IC_{50}$) obtained by a plot of cell-bound $^{125}$I-rhC5a versus concentration of unlabeled competitor (cf. FIG. 3, Table 1). The $ID_{50}$ of the C5a muteins (SEQ ID NO: 14-22) was determined as the concentration leading to inhibition of half-maximal enzyme release induced by $10^{-9}$ M rhC5a. The $ED_{50}$ value of C5a or C5a mutants was determined as the concentration leading to half-maximal enzyme release; i.e. the release of N-Acetyl-β-D-glucosaminidase from C5aR-RBL-cells as described in the examples. As can be taken from Table 1 no such enzyme release and thus no agonistic properties were observed for protein concentration of the C5a muteins (SEQ ID NO: 14-22) as high as $4\times10^{-6}$ M.

EXAMPLES

Generation of C5a Muteins

The C5a muteins depicted in Table 1 were constructed by PCR using the pJuFo ΔpIII-A8B mutant as vector [21]. First the Jun cassette was deleted by digesting the vector with XhoI and BamHI with 15 U per μg DNA at 37° C. for 1 hour. The digested, linearized vector fragment was run on an agarose gel, a band at the expected size was cut out and purified using glass milk beads. The purified fragment was religated. The 50 μl ligation reaction included 200 ng of digested vector and was incubated overnight at 15° C. with 640 U $T_4$-DNA ligase (Biolabs NEB). The new vector fragment pFo ΔpIII-A8B was yielded in which the Jun moiety is deleted. The deletion was confirmed by DNA sequencing. Next the Fos cassette within the pFo ΔpIII-A8B vector was deleted by digesting the vector with SacI and KpnI with 15 U per μg DNA at 37° C. for 1 hour. Again, the digested, linearized vector fragment was run on an agarose gel, a band at the expected size was cut out and purified using glass milk beads. This vector (pΔJuFo ΔpIII-A8B=pA8B) was then used as template to ligate the PCR fragments of the different C5a muteins, which were generated as follows:

To prepare C5a-(1-66, Cys27Ala)-A8B primers JK124 and JK116 were used. To prepare C5-(1-66, Cys27Ala)-A8B-Leu70 primers JK124 and JK146. To prepare C5a-(1-66, Cys27Ala)-Cys71 primers JK124 and JK148 were used. To prepare C5a-(1-66, Cys27Ala)-Cys73 primers JK124 and JK130 were used. To prepare C5-(1-66, Cys27Ala)-Leu70Tyr73 primers JK124 and JK126 were used. To prepare C5a-(1-66, Cys27Ala)-Lys69-Ala70 primers JK124 and JK147 were used. To prepare C5a-(1-66, Cys27Arg)-A8B primers JK 152 and JK 153 were used. To prepare C5a-(1-66, Ala27Cys)-A8B-Del.71-73 primers JK124 and JK149 were used. To prepare C5a-(1-66, Cys27Ala)-A8B-Ala69 primers JK124 and JK 154 were used. To prepare C5a-(1-66, Cys27Ala)-A8B-Asp69 primers JK124 and JK 156 were used. To prepare C5a-(1-66, Cys-3, Gly-2, -1, Cys27Ala)-A8B primers SEQ ID NO: 37 and JK 116 and were used. To prepare C5a-(1-66, Cys27Ala)-A5A primers JK 124 and SEQ ID NO:38 were used.

The different primers were the following from 5' to 3':

```
                                            (SEQ ID NO: 25)
JK124: GAG AGA GAG AGA GCT CAC GCT GCA AAA GAA GAT
       A;

(SEQ ID NO: 26)
JK116: CGA ATT GGG TAC CTT ATT AAC;

(SEQ ID NO: 27)
JK146: GAG AGA GAG AGG TAC CTT ATT AAC GCA ACA GCA
       GCC TTT TAA AAG;

(SEQ ID NO: 28)
JK148: GAG AGA GAG AGG TAC CTT ATT AAC ACG ACC TTT
       TAA AAG;

(SEQ ID NO: 29)
JK130: GAG AGA GAG AGG TAC CTT ATT AGC ACA ACA GCG
       ACC TTT TAA AAG;

(SEQ ID NO: 30)
JK126: GAG AGA GAG AGG TAC CTT ATT AAT ACA ACA GCA
       GCC TTT TAA AAG;

(SEQ ID NO: 31)
JK147: GAG AGA GAG AGG TAC CTT ATT AAC GCA ACA GCG
       ACT TTT TAA AAG;
```

-continued

JK152: GAG CCC GCG TTA ATA ATG ATG; (SEQ ID NO: 32)

JK153: CAT CGT AAC AAC ATT TCT TCA CTA C; (SEQ ID NO: 33)

JK149: GAG AGA GAG AGG TAC CTT ATT ACG ACC TTT AAA AAG; (SEQ ID NO: 34)

JK154: GAG AGA GAG AGG TAC CTT ATT AAC GCA ACA GCG ACG CTT TAA AAG; (SEQ ID NO: 35)

JK156: GAG AGA GAG AGG TAC CTT ATT AAC GCA ACA GCG AGT CTT TAA AAG AG; (SEQ ID NO: 36)

SEQ ID NO:37:
GAG AGA GAG AGA GCT CTG CGG TGG TAC GCT GCA AAA GAA GAT A

SEQ ID NO:38:
GAG AGA GAG AGG TAC CTT ATT AAT ACA GCA ACA ACA GTT TAA AAG

PCR reactions were performed in 100 µl volumes containing 1 pg template DNA pJuFo ΔpIII-A8B, 200 µM of each dNTP, 20 pmol of each primer, and reaction buffer supplied by the manufacturer (Stratagene). Reaction mixtures were overlaid with mineral oil and kept at 94° C. for 5 min (hot start) in a thermocycler. Then 5 U of Pfu polymerase (Stratagene) were added and the mixtures were cycled 30 times (94° C. 90 sec, 52° C. 120 sec, 72° C. 120 sec) followed by incubation at 72° C. for 10 min.

After phenol chloroform extraction and ethanol precipitation DNA fragments were digested with SacI and KpnI (Bioloabs, NEB) using 60 U per µg DNA at 37° C. for 1 hour. The ligation mix consisting of the linearized vector and the digested PCRs was heat inactivated at 70° C. for 30 min, purified by phenol chloroform extraction and ethanol precipitation, followed by resuspension in 5 µl TE. Two portions of 2.5 µl each were electroporated into E. coli TG1 cells (Stratagene) using a BioRad pulser set at 25 µF, 2.5 kV and 200Ω. Immediately after the pulse, 1 ml of freshly prepared SOC medium was added and the cells were grown for 1 hour at 37° C. and plated on TYE plates supplemented with 100 µg/ml ampicillin and 1% glucose (=TYE+amp+gluc). To score the total number of independent transformants 100 µl of appropriate dilutions were plated onto TYE+amp+gluc.

Preparation and Purification of C5a Muteins by Immune Affinity Chromatography

TG1 bacteria harboring the respective derivate of expression plasmid pA8B were grown in 2× TY+amp medium containing 100 µg/ml ampicillin and 0.1% glucose. At an OD$_{600}$ of 0.9, IPTG was added to give a final concentration of 0.5 mM. Bacteria were grown overnight with shaking at room temperature. The next day, the periplasmic fraction was prepared by freezing and thawing.

For purification CNBr activated sepharose (Pharmacia, Uppsala, Sweden) was coated with C5a specific mAb 561 ([39] following the manufacturers instructions. A small column (BIOGNOSIS, Jülich, Germany) was loaded with 100 µl gel matrix. The periplasmic fraction (400 µl diluted 1:5 with PBS) prepared from TG1 cells transformed with one of the C5a muteins was applied to the column for 1 h at 4° C. The column was washed with 2 ml PBS and subsequently loaded with a pre-elution buffer (10 mM phosphate buffer pH 6.8). Then the bound C5a mutein was eluted by shifting the pH to 2.5 using 100 mM glycin/HCl buffer. Ten 50 µl aliquots were collected and subsequently tested in a dot-blot with mAb 561. Positive fractions were pooled. The concentration of purified C5a muteins was determined by ELISA as described below.

To analyze the purity after immune-affinity-chromatography C5a muteins were separated by 0.1% SDS-15% PAGE using a mini-gel twin chamber (Biometra, Göttingen, Germany) and silver stained (see FIG. 2). Judging from the silver stain, the muteins of the invention were purified to homogeneity. In the case of the mutein C5a-(1-66, Cys-3, Gly-2, -1, Cys27Ala)-A8B PAGE analysis under reducing and non-reducing conditions revealed that spontaneous dimerization via formation of disulfide bridges of the C-terminal Cys residue occurred in the oxidizing milieu of the periplasm of E. coli (data not shown).

ELISA to Determine the Concentration of Purified C5a Muteins

Mab 561 was diluted to 10 µg/ml in PBS and was coated overnight at 22° C. to a polystyrene microtiter plate (Greiner, Germany). Then the plates were rinsed 3 times in PBS and saturated with PBS containing 2% non fat dry milk for 60 min at 37° C. After washing 3× with 50 mM Tris buffer, 0.15 M NaCl, pH 7.5 (TRIS), 50 µl of the purified C5a muteins diluted in 50 mM Tris buffer, 0.15 M NaCl, pH 7.5 supplemented with 10% non fat dry milk powder (TRIS-Milk) were added. After incubation for 90 min at 22° C. plates were washed 4× with TRIS and subsequently incubated with 50 µl of biotinylated anti C5a mAb 557 (10 µg/ml) diluted in TRIS-Milk for 90 min at 22° C. Plates were washed 4× with 50 mM TRIS. Subsequently, 50 µl of avidin-alkaline-phosphatase diluted in TRIS was added and incubated for 30 min at 22° C. Plates were developed with p-nitrophenolphosphate (1 mg/ml diluted in diethanolamine, 5 mM MgCl$_2$, pH 9).

Competitive Binding Study

For competitive binding studies, 40 µl of a reaction mixture containing a constant amount of $^{125}$I-rhC5a as tracer (≈17000 cpm) and increasing concentrations of unlabeled C5a muteins were incubated in a microtiter plate on ice. The tracer concentration was thus less than ¹⁄₁₀ of the Kd of recombinant human C5a which is a prerequisite for evaluating of correct IC$_{50}$ values. The binding reaction was started by adding 25 µl of ice-cold RBL-C5aR cell suspension. After incubation on ice for 30 min, cell bound and free $^{125}$I-rhC5a were separated by filtration of 60 µl through a microtitration-membrane plate (Multiscreen™-HV; 0.45 µm, MAHV N45, Millipore) using a vacuum manifold (Millipore). The wells were washed out once with 100 µl HAG-CM buffer (20 mM HEPES pH 7.4, 125 mM NaCl, 5 mM KCl, 1 mM CaCl$_2$, 1 mM MgCl$_2$, 0.25% BSA and 0.5 mM glucose), dried by a heat lamp and punched out with a membrane punch assembly (Millipore). Punched out membranes were counted in a γ-counter (Packard, Canberra). The plot of cell-bound $^{125}$I-rhC5a versus concentration of unlabeled competitor yields the half-maximal inhibitory concentrations (IC$_{50}$) (cf. FIG. 3, Table 1).

Glucosaminidase Release from Human C5a Receptor Transfected RBL-Cells (C5aR-RBL-Cells)

The release of N-Acetyl-β-D-glucosaminidase from C5aR-RBL-cells was determined as described [40]. The ED$_{50}$ of C5a or C5a mutants was determined as the concentration leading to half-maximal enzyme release. The antagonistic potency of the C5a muteins was tested by the capacity of C5a muteins to inhibit the release of N-Acetyl-β-D-glucosaminidase from C5aR-RBL-cells induced by $10^{-9}$ M C5a. Briefly, 75 µl/well of C5aR-RBL cells ($2×10^6$/ml) were suspended in HAG-CM buffer (20 mM HEPES, 125 mM NaCl, 5 mM KCl, 1 mM CaCl$_2$, 1 mM MgCl$_2$, 0.25% BSA and 0.5 mM glucose, pH 7.4) and equilibrated for 5 min at 37° C. Meanwhile, 20 µl of serial dilutions of the purified C5a mutein were transferred to a PS-microtiter plate (Greiner, Germany) and incubated for 5 min at 37° C. After 5 min pre-incubation, cytochalasin B (20 µg/ml) was added to the cells and incubated for 3 min at 37° C. Subsequently, the cells were transferred to the C5a muteins and incubated for 10 min at 37° C. Then C5a was added at a final concentration of $10^{-9}$ M and the reaction was allowed to proceed for 5 min at 37° C. The reaction was stopped by centrifugation at 1157 g for 3 min at 4° C. Subsequently, 75 µl of the supernatant were mixed with 100 µl substrate (p-nitrophenyl-N-acetyl-β-D-glucosaminide). The reaction was stopped by adding 75 µl glycine/NaOH, pH 10.4/well, The absorbance (405 nm) was determined in a Titertek-Multiscan ELISA reader. The ID$_{50}$ of the C5a muteins (SEQ ID NO: 14-22) was determined as the concentration leading to inhibition of half-maximal enzyme release induced by $10^{-9}$ M rhC5a, showing the antagonistic properties of the muteins of the invention.

[10] Bautsch et al., Biochem. J. 288, p. 261-266, 1992
[11] Haslett et al., J. Immunol. 14, p. 3510-3517, 1989
[12] Krug, N. et al, Am. J. Respir. Crit. Care Med., 164:1841-1843, 2001
[13] Mollison et al., Proc. Natl. Acad. Sci. USA, 86:292-296, 1989
[14] U.S. Pat. No. 5,942,599
[15] U.S. Pat. No. 5,696,230
[16] WO 99/00406
[17] U.S. Pat. No. 5,807,824
[18] Pellas et al., J. Immunol., p. 561-5621, 1998
[19] Hennecke M., Untersuchung zur C5a-C5a Rezeptor-Interaktion unter Verwendung des Phage-Displays, PhD thesis, Medical School Hannover, 1998
[20] Hennecke et al., Eur. J. Biochem. 252, p. 36-44, 1998
[11] Heller et al., J. Immunol., 163, p. 985-994 1999.
[22] Baumann, U. et al, J. Immunol., 164: 1065-1070, 2000
[23] Köhl, The anaphylatoxins, in Complement: a practical approach (Dodds A. W. & Simm R. B, Eds., p. 135-163, IRL press, Oxford, 1997
[24] Toth, M. J. et al., Prot. Science, 3: 1159-1168, 1994
[25] Bock et al. Eur. J. Immunol., 27, pp 1522-1529, 1997
[26] Seligmann et al., Agents and Actions 21, p. 375-378, 1987
[27] Cain et al. J. Immunol. Methods, 245: 139-145, 2000
[28] U.S. Pat. No. 5,506,121

TABLE 1

Binding and functional properties of generated C5a mutants

| Position in C5a | 67 | 68 | 69 | 70 | 71 | 72 | 73 | 74 | IC$_{50}$ [nM] | ID$_{50}$ [nM] | ED$_{50}$ [nM] |
|---|---|---|---|---|---|---|---|---|---|---|---|
| rhC5a | H | K | D | M | Q | L | G | R | 2.7 ± 0.2 (n = 4) | — | 3.5 ± 0.3 (n = 5) |
| C5a-(1-66,Cys27Ala)-A8B | F | K | R | S | L | L | | R | 35.4 ± 3.4 (n = 4) | 22.3 ± 2.1 (n = 3) | >4 × $10^{3*}$ (n = 3) |
| C5a-(1-66,Cys27Ala)-A8B-Leu70 | F | K | R | L | L | L | | R | 23.1 ± 2.6 (n = 3) | 7.9 ± 0.5 (n = 3) | >4 × $10^{3*}$ (n = 3) |
| C5a-(1-66,Cys27Ala)-A8B-Cys71 | F | K | R | S | C | | | | n.d. | 99.2 ± 5.3 (n = 3) | >4 × $10^{3*}$ (n = 3) |
| C5a-(1-66,Cys27Ala)-A8B-Cys73 | F | K | R | S | L | L | | C | 37.3 ± 2.3 (n = 3) | 17.4 ± 0.9 (n = 3) | >4 × $10^{3*}$ (n = 3) |
| C5a-(1-66,Cys27Ala)-A8B-Leu70-Tyr73 | F | K | R | L | L | L | | Y | 21.3 ± 1.3 (n = 5) | 8.8 ± 0.4 (n = 3) | >4 × $10^{3*}$ (n = 3) |
| C5a-(1-66,Cys27Ala)-A8B-Lys69-Ala70 | F | K | K | A | L | L | | R | n.d. | 60.8 ± 4.4 (n = 3) | >4 × $10^{3*}$ (n = 3) |
| C5a-(1-66,Cys27Arg)-A8B | F | K | R | S | L | L | | R | 43.1 ± 2.2 (n = 4) | 17.5 ± 0.6 (n = 3) | >4 × $10^{3*}$ (n = 3) |
| C5a-(1-66,Cys27Ala)-A8B-Del.71-73 | F | K | R | S | | | | | 26.9 ± 1.8 (n = 3) | 17.4 ± 0.7 (n = 3) | >4 × $10^{3*}$ (n = 3) |
| C5a-(1-66,Cys-3,Gly-2,-1,Cys27Ala)-A8B | F | K | R | S | L | L | | R | n.d. | 65.3 ± 2.8 (n = 3) | >2 × $10^{3*}$ (n = 3) |
| C5a-(1-66,Cys27Ala)-A8B-Ala69 | F | K | A | S | L | L | | R | 30.1 ± 2.4 (n = 4) | — | 36.8 ± 2.9 (n = 3) |
| C5a-(1-66,Cys27Ala)-A8B-Asp69 | F | K | D | S | L | L | | R | 5.4 ± 0.7 (n = 3) | — | 5.9 + 0.4 (n = 3) |
| C5a-(1-66,Cys27Ala)-A5A | F | K | L | L | L | L | | R | n.d. | 124 (n = 2) | >2 × $10^{3*}$ (n = 2) |

*highest concentration which was used in the assay,
n = number of experiments,
n.d. = not determined

THE FOLLOWING REFERENCES ARE CITED IN THIS APPLICATION

[1] Kinoshita, Immunology Today 12, p. 291-300, 1991
[2] Müller-Eberhard, Annu. Rev. Biochem. 57, p. 321-347, 1988
[3] Gerard, C. & Gerard, N. P., Annu. Rev. Immunol. 12, p. 775, 1994
[4] Köhl J., & Bitter-Suemann, Anaphylatoxins in Complement in Health and Disease, $2^{nd}$ Ed. K. Whaley, M. Loos and J. M. Weiler, Eds. Kluwer Academic Publisher, Dordrecht, p. 295, 1993
[5] Ember et al., Characterization of complement anaphylatoxins and their biological D responses in The Human Complement in Health and Disease. J. Volankis and M. M. Frank, Eds, Marcel Dekker, New York, p. 241-284, 1998
[6] Czermak, B. J et al., Nat. Medicine, 5: 788-792, 1999
[7] Bautsch, W et al., J. Immunol., 165: 5401-5405, 2000
[8] Humbles et al., Nature, 406: 998-991, 2000
[9] Karp, C. L. et al, Nature Immunol., 1:221-226, 2000
[29] U.S. Pat. No. 6,022,951
[30] Handbook of Fluorescent Probes and Research Chemicals, p, 69, $6^{th}$ Ed., R. Haugland, Molecular Probes.
[31] Remington et al., Pharmaceutical Sciences, 15th Ed., Mack Pub., Easton 1975
[32] Baneyx F., Curr. Opin. Biotechnol. 1999, 10: 411-21,
[33] Makrides S C, Prot. Expr. Purif. 17: 183-202, 1999
[34] Cereghino, J L, and Cregg J M. FEMS Microbiol. Rev. 2000, 24: 45-66;
[35] Colosimo A. et al., Biotechniques 29: 314-318, 2000
[36] Bautsch et al., Immunobiology 185, 41-52 1992
[37] Crameri, R. and Suter M., Gene 137, 69-75, 1993
[38] Barbas et al., Proc. Natl. Acad. Sci. USA, 88, 7978-7982, 1991
[39] Klos, A. et al., J. Immunol. Methods, 111: 241-252, 1988
[40] Hennecke, M. et al., Gene, 184: 262-272, 1997

The invention claimed is:

1. A mutein of the C5a anaphylatoxin which is a C5a receptor antagonist and which comprises a Cys27Ala mutation at position 27 and a C-terminal amino acid sequence wherein the amino acid residue naturally occurring at position 69 is mutated wherein the numbering of the amino acid sequence refers to the amino acid position defined by SEQ ID NO 13;

wherein the C-terminal amino acid sequence is selected from SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, wherein the C-terminal amino acid sequence begins at position 67 with reference to SEQ ID NO 13; and wherein the fusion proteins of the mutein of SEQ ID NO: 14 with Jun/Fos and/or with Jun/Fos and the minor coat protein of the filamentous M13 phage fused to the N-terminus of the mutein are excluded.

2. A C5a receptor antagonist comprising a human C5a anaphylatoxin comprising an amino acid sequence selected from the group consisting of SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; and SEQ ID NO:39.

3. A C5a receptor antagonist according to claim 2 further comprising an N-terminal linker sequence which is capable of dimerizing the C5a mutein.

4. A C5a receptor antagonist according to claim 3, wherein the N-terminal linker sequence comprises the sequence Cys-Gly-Gly or SEQ ID NO: 48.

5. A C5a receptor antagonist according to claim 2 which is conjugated to a moiety which enhances the in vivo half-life of the mutein.

6. A pharmaceutical composition comprising a C5a receptor antagonist of claim 2 and a pharmaceutically acceptable carrier.

7. A method of inhibiting C5a in a patient having inflammation, comprising the step of administering a pharmaceutical composition comprising a mutein of claim 1, or a C5a receptor antagonist of 15 and a pharmaceutically acceptable carrier to a mammal in need thereof.

8. A mutein of SEQ ID NO 13 which is a C5a receptor antagonist and which comprises a mutation at position 27 selected from Cys27Ala and Cys27Arg, wherein the numbering of the position is defined by SEQ ID NO: 13, and a C-terminal amino acid sequence selected from SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, wherein the C-terminal amino acid sequence begins at position 67 with reference to SEQ ID NO 13.

9. A mutein according to claim 1 further comprising an N-terminal linker sequence which is capable of dimerizing the C5a mutein.

10. A mutein according to claim 9, wherein the N-terminal linker sequence comprises the sequence Cys-Gly-Gly or SEQ ID NO: 48.

11. A mutein according to claim 1 which is conjugated to a moiety which enhances the in vivo half-life of the mutein.

12. A pharmaceutical composition comprising a mutein of claim 1 and a pharmaceutically acceptable carrier.

* * * * *